United States Patent
Shelton, IV et al.

(10) Patent No.: US 12,102,445 B2
(45) Date of Patent: Oct. 1, 2024

(54) MONITORING AND COMMUNICATING INFORMATION USING DRUG ADMINISTRATION DEVICES

(71) Applicant: Janssen Pharmaceuticals, Inc., Titusville, NJ (US)

(72) Inventors: Frederick E. Shelton, IV, Hillsboro, OH (US); Monica A. Kapil, San Jose, CA (US); Emma L. Hubert, San Jose, CA (US); Jason L. Harris, Lebanon, OH (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 1024 days.

(21) Appl. No.: 17/068,865

(22) Filed: Oct. 13, 2020

(65) Prior Publication Data
US 2021/0345953 A1    Nov. 11, 2021

Related U.S. Application Data

(60) Provisional application No. 63/020,940, filed on May 6, 2020, provisional application No. 63/020,925, filed
(Continued)

(51) Int. Cl.
*A61B 5/00* (2006.01)
*A61B 5/0205* (2006.01)
(Continued)

(52) U.S. Cl.
CPC .......... *A61B 5/4839* (2013.01); *A61B 5/0022* (2013.01); *A61B 5/02055* (2013.01); *A61B 5/1101* (2013.01); *A61B 5/1112* (2013.01); *A61B 5/1118* (2013.01); *A61B 5/14532* (2013.01); *A61B 5/14542* (2013.01); *A61B 5/4266* (2013.01); *A61B 5/4866* (2013.01); *A61M 5/1723* (2013.01); *A61M 5/2033* (2013.01); *A61M 15/0065* (2013.01); *A61M 15/08* (2013.01); *G16H 10/60* (2018.01); *G16H 20/10* (2018.01); *G16H 20/30* (2018.01);
(Continued)

(58) Field of Classification Search
None
See application file for complete search history.

(56) References Cited

U.S. PATENT DOCUMENTS

| | | |
|---|---|---|
| 4,946,069 A | 8/1990 | Fuchs |
| 5,363,842 A | 11/1994 | Mishelevich et al. |

(Continued)

FOREIGN PATENT DOCUMENTS

| | | |
|---|---|---|
| EP | 3539593 A1 | 9/2019 |
| EP | 3669912 A1 | 6/2020 |
| WO | WO-2021059210 A1 | 4/2021 |

OTHER PUBLICATIONS

"Diet Coke and Mentos Explained," Weebly, dated no later than Mar. 16, 2020, 2 pages (available at <https://dietcoke-and-mentos.weebly.com/>).
(Continued)

*Primary Examiner* — Manuel A Mendez
(74) *Attorney, Agent, or Firm* — Mintz Levin Cohn Ferris Glovsky and Popeo, P.C.

(57) ABSTRACT

In general, systems and methods for monitoring and communicating information using drug administration devices are provided.

15 Claims, 14 Drawing Sheets

Related U.S. Application Data on May 6, 2020, provisional application No. 63/020,928, filed on May 6, 2020.

(51) Int. Cl.
| | |
|---|---|
| *A61B 5/11* | (2006.01) |
| *A61B 5/145* | (2006.01) |
| *A61M 5/172* | (2006.01) |
| *A61M 5/20* | (2006.01) |
| *A61M 15/00* | (2006.01) |
| *A61M 15/08* | (2006.01) |
| *G16H 10/60* | (2018.01) |
| *G16H 20/10* | (2018.01) |
| *G16H 20/30* | (2018.01) |
| *G16H 20/40* | (2018.01) |
| *G16H 20/60* | (2018.01) |
| *G16H 40/20* | (2018.01) |
| *G16H 40/40* | (2018.01) |
| *G16H 40/67* | (2018.01) |
| *G16H 50/30* | (2018.01) |
| *G16H 70/40* | (2018.01) |
| *H04W 12/02* | (2009.01) |
| *H04W 12/0431* | (2021.01) |
| *A61B 5/021* | (2006.01) |
| *A61B 5/024* | (2006.01) |

(52) U.S. Cl.
CPC .............. *G16H 20/40* (2018.01); *G16H 20/60* (2018.01); *G16H 40/20* (2018.01); *G16H 40/40* (2018.01); *G16H 40/67* (2018.01); *G16H 50/30* (2018.01); *G16H 70/40* (2018.01); *H04W 12/02* (2013.01); *H04W 12/0431* (2021.01); *A61B 5/021* (2013.01); *A61B 5/024* (2013.01); *A61B 2560/0242* (2013.01); *A61M 2205/3317* (2013.01); *A61M 2205/3327* (2013.01); *A61M 2205/3553* (2013.01); *A61M 2205/3584* (2013.01); *A61M 2205/50* (2013.01); *A61M 2205/502* (2013.01); *A61M 2205/505* (2013.01); *A61M 2205/52* (2013.01); *A61M 2230/04* (2013.01); *A61M 2230/20* (2013.01); *A61M 2230/201* (2013.01); *A61M 2230/50* (2013.01); *A61M 2230/63* (2013.01)

(56) References Cited

U.S. PATENT DOCUMENTS

| | | | |
|---|---|---|---|
| 6,321,942 B1 | 11/2001 | Krampen et al. | |
| 7,299,949 B2 | 11/2007 | Greiner-Perth | |
| 7,938,796 B2 * | 5/2011 | Moubayed ............. | G16H 40/67 604/153 |
| 8,585,659 B2 | 11/2013 | Shay | |
| 8,696,616 B2 | 4/2014 | Baynham et al. | |
| 9,129,054 B2 | 9/2015 | Nawana et al. | |
| 9,168,000 B2 | 10/2015 | Dunki-Jacobs et al. | |
| 9,314,808 B2 | 4/2016 | Allsop | |
| 9,427,580 B2 | 8/2016 | Bork et al. | |
| 9,555,950 B2 | 1/2017 | Le Maner et al. | |
| 9,984,211 B2 | 5/2018 | Hsu | |
| 10,456,534 B2 | 10/2019 | Reisacher et al. | |
| 10,569,071 B2 | 2/2020 | Harris et al. | |
| 10,733,267 B2 * | 8/2020 | Pedersen ............. | A61B 5/4821 |
| 2002/0014951 A1 | 2/2002 | Kramer et al. | |
| 2002/0042596 A1 | 4/2002 | Hartlaub et al. | |
| 2002/0077852 A1 | 6/2002 | Ford et al. | |
| 2002/0091454 A1 | 7/2002 | Vasko | |
| 2005/0027791 A1 | 2/2005 | Bos et al. | |
| 2007/0251835 A1 | 11/2007 | Mehta et al. | |
| 2008/0139907 A1 | 6/2008 | Rao et al. | |
| 2008/0154177 A1 | 6/2008 | Moubayed et al. | |
| 2009/0069787 A1 | 3/2009 | Estes et al. | |
| 2011/0004188 A1 | 1/2011 | Shekalim | |
| 2011/0295337 A1 | 12/2011 | Albrecht et al. | |
| 2012/0330684 A1 | 12/2012 | Jacobs et al. | |
| 2014/0243635 A1 | 8/2014 | Arefieg | |
| 2015/0274344 A1 | 10/2015 | Sullivan et al. | |
| 2015/0297845 A1 | 10/2015 | Shahaf et al. | |
| 2016/0045674 A1 | 2/2016 | Blei et al. | |
| 2016/0324845 A1 | 11/2016 | Myers et al. | |
| 2017/0124284 A1 | 5/2017 | McCullough et al. | |
| 2017/0286610 A9 | 10/2017 | Harris et al. | |
| 2018/0028755 A1 | 2/2018 | Philip et al. | |
| 2018/0060527 A1 | 3/2018 | Kalyanpur et al. | |
| 2018/0189638 A1 | 7/2018 | Nurvitadhi et al. | |
| 2018/0214077 A1 | 8/2018 | Dunki-Jacobs et al. | |
| 2018/0261310 A1 | 9/2018 | Edwards et al. | |
| 2018/0261322 A1 | 9/2018 | Cheng et al. | |
| 2018/0361085 A1 | 12/2018 | Malhotra et al. | |
| 2019/0054250 A1 | 2/2019 | Amschler et al. | |
| 2019/0200844 A1 | 7/2019 | Shelton, IV et al. | |
| 2019/0200981 A1 | 7/2019 | Harris et al. | |
| 2019/0201046 A1 | 7/2019 | Shelton, IV et al. | |
| 2019/0201114 A1 | 7/2019 | Shelton, IV et al. | |
| 2019/0201140 A1 | 7/2019 | Yates et al. | |
| 2019/0205002 A1 | 7/2019 | Colister et al. | |
| 2019/0206004 A1 | 7/2019 | Shelton, IV et al. | |
| 2019/0206555 A1 | 7/2019 | Morgan et al. | |
| 2019/0207857 A1 | 7/2019 | Shelton, IV et al. | |
| 2019/0231707 A1 | 8/2019 | Stiles et al. | |
| 2019/0321566 A1 | 10/2019 | Leonardi et al. | |
| 2019/0336682 A1 | 11/2019 | Colleran et al. | |
| 2020/0054214 A1 | 2/2020 | Govari | |
| 2021/0322018 A1 | 10/2021 | Shelton, IV et al. | |
| 2021/0345954 A1 | 11/2021 | Shelton, IV et al. | |

OTHER PUBLICATIONS

"Dual Component Epoxy Cartridges K-Series Syringe," Adhesive Dispensing Ltd., dated no later than Mar. 21, 2020, 2 pages (available at <https://www.adhesivedispensing.net/Dual_Component_K_Series_Dispensing_s/236.htm>).

"Molecular Sieve vs Silica Gel: What's the Difference?", Multisorb Fixation Group, dated no later than Mar. 24, 2020, 2 pages (available at <https://www.multisorb.com/blog/pharmaceuticals/molecular-sieve-vs-silica-gel-whats-the-difference/>).

"Orbeez® Toys—Add Water to Make Them Grow!", Maya Toys, dated no later than Mar. 24, 2020, 2 pages (available at <https://mayatoys.net/pages/orbeez>).

"Philips Medication Dispenser," Philips Lifeline, dated no later than Mar. 17, 2020, 6 pages (available at <https://www.lifeline.philips.com/pill-dispenser/health-mdp.html>).

"Study Shows High Altitude and Medication May Not Mix," healthNEWS, University of Cincinnati Academic Health Center, Jan. 14, 1999, 1 page (available at <http://healthnews.uc.edu/news/?/153/>).

"The Companion Dual Chamber Reconstitution Syringe," Credence MedSystems, Inc, dated no later than Mar. 18, 2020, 3 pages <available at <https://www.credencemed.com/dual-chamber/>).

"VapourSoft® Technology," Bespak Europe Ltd., dated no later than Mar. 16, 2020, 2 pages (available at <https://bespak.com/products/injection-devices/vapoursoft-technology/>).

Jae Hung Park et al., "Biodegradable Polymers for Microencapsulation of Drugs," Molecules 2005, 10, p. 146-161.

Man Chiu Fung, "Experimental and numerical study of spray characteristics of nasal spray devices," School of Aerospace, Mechanical and Manufacturing Engineering Science, Engineering and Technology Portfolio, RMIT University, Aug. 2013 (179 pages).

Rafi, "14 List Of Chemicals That Glow Under Black Light—Application," Jan. 24, 2018, 3 pages (available at <https://azchemistry.com/list-of-chemicals-that-glow-under-black-light>).

International Preliminary Report on Patentability for International Patent Application No. PCT/IB2021/058427 mailed on Apr. 5, 2022. (20 pages).

(56) References Cited

OTHER PUBLICATIONS

International Search Report for International Patent Application No. PCT/IB2021/058427 mailed on Apr. 5, 2022. (9 pages).
U.S. Appl. No. 17/221,107, filed Apr. 2, 2021, Frederick E. Shelton et al.

* cited by examiner

MONITORING AND COMMUNICATING INFORMATION USING DRUG ADMINISTRATION DEVICES

CROSS REFERENCE TO RELATED APPLICATIONS

The present application claims priority to U.S. Prov. App. No. 63/020,940 entitled "Drug Administration Devices That Communicate With External Systems And/Or Other Devices" filed May 6, 2020, U.S. Prov. App. No. 63/020,925 entitled "Remote Aggregation Of Data For Drug Administration Devices" filed May 6, 2020, and U.S. Prov. App. No. 63/020,928 entitled "Interconnection Of Drug Administration Systems" filed May 6, 2020, which are hereby incorporated by reference in their entireties.

FIELD

The present disclosure relates generally to monitoring and communicating information using drug administration devices.

BACKGROUND

Pharmaceutical products (including large and small molecule pharmaceuticals, hereinafter "drugs") are administered to patients in a variety of different ways for the treatment of specific medical indications. Regardless of the manner of the administration, care must be taken when administering drugs to avoid adverse effects on the patient. For example, care must be taken not to administer more than a safe amount of the drug to the patient. This requires consideration of the amount of dose given and the time frame over which the dose is delivered, sometimes in relation to previous doses, or doses of other drugs. Moreover, care must be taken not to inadvertently administer an incorrect drug to the patient, or drugs that have degraded due to their age or storage conditions. All of these considerations can be conveyed in guidance associated with the specific drugs or drug combinations. However, this guidance is not always followed correctly, for example due to mistakes, such as human error. This can lead to adverse effects on the patient or result in inappropriate drug administration, for example insufficient or excessive volume of drug being administered for the specific medical indication.

Patients rarely share the same medical characteristics. For example, patients generally have different ages, weights, general states of health, and medical histories. Therefore the same illness tends to affect patients differently. Thus, while guidance supplied with specific drugs may aid a medical practitioner or patient in determining a suitable dosage amount, dosage frequency, and dosage time (dosage regimen) it will not necessarily inform the medical practitioner or patient of the optimum dosage for a particular patient. In order to determine the optimum dosage, the medical practitioner or patient would have to measure some or all possible factors affecting a patient and consider how the different factors interact. This is often impossible, and so medical practitioners or patients have to make a best guess as to the optimum dosage based on information that they have observed about the patient. These best guesses will rarely result in timely administration of an optimum dosage. Moreover, because the best guess is based on data observed by the medical practitioner or patient, there is an undesirable element of subjectivity and possibility of user error when determining or attempting to administer the best guess dosage.

In relation to how a drug is administered to the patient, there are various dosage forms that can be used. For example, these dosage forms may include parenteral, inhalational, oral, ophthalmic, topical, and suppository forms of one or more drugs.

The dosage forms can be administered directly to the patient via a drug administration device. There are a number of different types of drug administration devices commonly available for delivery of the various dosage forms including: syringes, injection devices (e.g., autoinjectors, jet injectors, and infusion pumps), and inhalers.

SUMMARY

In general, systems and methods for monitoring and communicating information using drug administration devices are provided.

In one aspect, a surgical system is provided that in one embodiment includes a surgical hub including a communications interface configured to wirelessly receive data during performance of a surgical procedure on a patient, and a drug administration device configured to deliver a drug therefrom to the patient. The drug administration device includes a sensor configured to sense information relating to a condition of the patient, and a memory configured to store data therein. The stored data includes a key established with a surgical hub and that is unique to the drug administration device and the surgical hub. The drug administration device also includes a communications interface configured to wirelessly transmit data indicative of the sensed information to the communications interface of the surgical hub, and a processor configured to use the key to anonymize the data indicative of the sensed information prior to the transmission of the data indicative of the sensed information.

The surgical system can vary in any number of ways. For example, the condition can be at least one of a physiological condition of the patient and a situational condition of the patient. For another example, the condition can be at least one of blood sugar level, blood pressure, perspiration level, heart rate, core temperature, tremor detection, time of day, date, patient activity level, blood pressure, metabolic rate, altitude, temperature of the drug, viscosity of the drug, geographic location information, angular rate, current of a motor used in delivering the drug, blood oxygenation level, sun exposure, osmolality, and air quality. For yet another example, the condition can be at least one of a geographic location of the patient and an orientation of the patient. For still another example, the condition can be at least one of a condition of the drug administration device and a condition of the drug.

For another example, the condition can include intake of food and/or drink by the patient. In at least some embodiments, the memory can also be configured to store therein an algorithm including at least one variable parameter, and the processor can also be configured to control delivery of a first dose of the drug from the drug administration device to the patient by executing the algorithm, change the at least one variable parameter of the algorithm stored in the memory based on the data gathered by the sensor regarding the intake of food and/or drink by the patient so a second dose of the drug is coordinated with a meal time of the patient, and, after changing the at least one variable parameter, control delivery of the second dose of the drug from the drug administration device to the patient by executing the algorithm.

For yet another example, the communications interface of the drug administration device can be configured to transmit the data during the performance of the surgical procedure, and the surgical hub can also include a processor configure to analyze, during the performance of the surgical procedure, the data received by the communications interface of the surgical hub. In at least some embodiments, the processor of the surgical hub can be configured to provide, during the performance of the surgical procedure, a notification to a user of the surgical hub indicative of the analysis. In at least some embodiments, the condition can be at least one of a physiological condition of the patient and a situational condition of the patient, and the notification can indicate that the data exceeds a predetermined threshold for the condition.

For still another example, the processor of the drug administration device can be configured to provide a notification to a user of the drug administration device, and the notification can indicate that the data exceeds a predetermined threshold for the condition. For yet another example, the surgical hub can include a server configured to be located local to, external to, and separate from the drug administration device. For another example, the communications interface of the surgical hub can be configured to wirelessly transmit data indicative of the received data to a cloud-based server configured to be remotely located from the drug administration device and from the surgical hub, the cloud-based server including a communications interface configured to receive the data transmitted by the communications interface of the surgical hub. For yet another example, the drug administration device can be configured to deliver the drug therefrom to the patient during performance of the surgical procedure on the patient, the sensor can be configured to sense information relating to the condition of the patient during the performance of the surgical procedure, and the communications interface can be configured to wirelessly transmit the data indicative of the sensed information to the communications interface of the surgical hub during the performance of the surgical procedure.

In another embodiment, a surgical system includes a drug administration device and a cloud-based server. The drug administration device is configured to deliver a drug therefrom to the patient, and the drug administration device includes a memory configured to store data therein including at least history of drug administrations from the drug administration device and a prescribed dosage schedule for drug administrations from the drug administration device, and a communications interface configured to wirelessly transmit data indicative of the data stored in the memory. The cloud-based server includes a communications interface configured to wirelessly receive the data transmitted by the communications interface of the drug administration device, a memory configured to store the received data therein and to store other data therein including at least information regarding surgery performed on the patient, and a processor configured to allow access to the received data and the other stored data by each of a plurality of users that include medical professionals, the plurality of medical professionals including a health care provider that prescribed the drug and/or the drug administration device to the patient, and at least one other health care provider.

The surgical system can have any number of variations. For example, the communications interface of the drug administration device can be configured to selectively transmit the data directly to the communications interface of the cloud-based server, and to the communications interface of the cloud-based server via a communications interface of a surgical hub. For another example, the other data can include at least one of physical limitation instructions for the patient including any one or more of physical therapy regimes of the patient, physical therapy limits of the patient, secondary medication limits for the patient, and physiologic interpretation aspects that could result from the surgery and/or the drug administrated to the patient. For yet another example, the other data can include instructions-for-use regarding at least one of how to administer the drug to the patient from the drug administration device, when to administer the drug to the patient from the drug administration device, how to monitor drug delivery to the patient from the drug administration device, how to return the patient to physical activity after the surgery, how much activity for the patient is appropriate after the surgery, one or more activities to suggest to the patient to perform after surgery, and one or more activities to instruct to the patient are prohibited after surgery. For still another example, the cloud-based system can be configured to automatically update the at least history of drug administrations from the drug administration device and the prescribed dosage schedule for drug administrations from the drug administration device based on input to the cloud-based system by a user including at least one of the health care provider that prescribed the drug and/or the drug administration device to the patient, and a manufacturer of the drug.

In another aspect, a surgical method is provided that in one embodiment includes sensing, using a sensor of a drug administration device, information relating to a condition of a patient. The drug administration device is configured to deliver a drug therefrom to the patient, includes a memory configured to store data therein including a key established with a surgical hub and that is unique to the drug administration device and the surgical hub, a communications interface configured to wirelessly transmit data indicative of the sensed information to the communications interface of the surgical hub, and a processor configured to use the key to anonymize the data indicative of the sensed information. The surgical method also includes anonymizing, using the processor of the drug administration device, the data indicative of the sensed information. The surgical method also includes wirelessly transmitting, using the communications interface of the drug administration device, the anonymized data to the surgical hub. The surgical hub includes a communications interface configured to wirelessly receive data during performance of a surgical procedure. The surgical method can have any number of variations.

BRIEF DESCRIPTION OF DRAWINGS

The present invention is described by way of reference to the accompanying figures which are as follows.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Examples of various types of drug administration devices, namely: an autoinjector 100, an infusion pump 200, and an inhaler 300, are described below.

Autoinjectors

Figure 1:
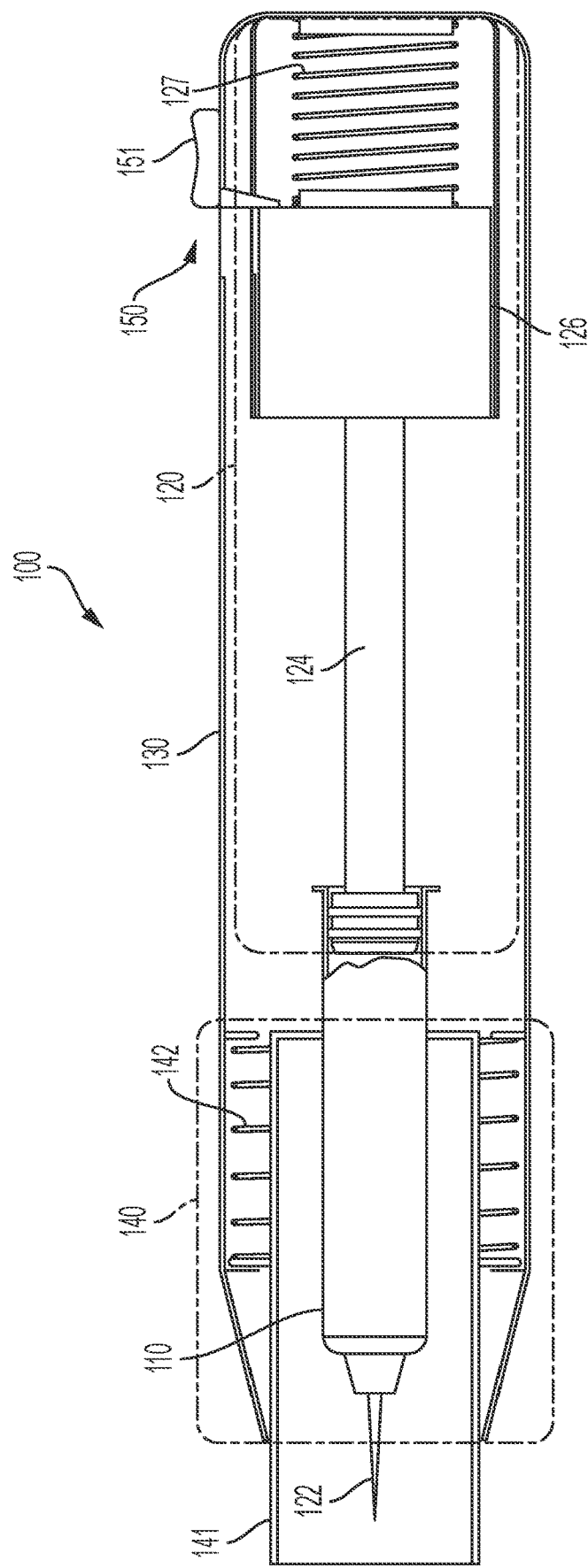
FIG. 1 is a schematic view of one embodiment of a first type of drug administration device, namely an autoinjector.

FIG. 1 is a schematic exemplary view of a first type of drug delivery device (also referred to herein as a "drug administration device"), namely an injection device, in this example an autoinjector 100, useable with embodiments described herein. The autoinjector 100 includes a drug holder 110, which retains a drug to be dispensed, and a dispensing mechanism 120, which is configured to dispense a drug from the drug holder 110 so that it can be administered to a patient. The drug holder 110 is typically in the form of a container which contains the drug, for example it may be provided in the form of a syringe or a vial, or be any other suitable container which can hold the drug. The autoinjector 100 includes a discharge nozzle 122, for example a needle of a syringe, which is provided at a distal end of the drug holder 110. The dispensing mechanism 120 includes a drive element 124, which itself may also include a piston and/or a piston rod, and drive mechanism 126. The dispensing mechanism 120 is located proximal to the end of the drug holder 110 and towards the proximal end of the autoinjector 100.

The autoinjector 100 includes a housing 130 which contains the drug holder 110, the drive element 124, and the drive mechanism 126 within the body of the housing 130, as well as containing the discharge nozzle 122, which, prior to injection, would typically be contained fully within the housing 130, but which would extend out of the housing 130 during an injection sequence to deliver the drug. The dispensing mechanism 120 is arranged so that the drive element 124 is advanced through the drug holder 110 in order to dispense the drug through the discharge nozzle 122, thereby allowing the autoinjector 100 to administer a drug retained in drug holder 110 to a patient. In some instances, a user may advance the drive element 124 through the drug holder 110 manually. In other instances, the drive element 124 may be advanced through the drug holder 110 under control of a robotic surgical system. In other instances, the drive mechanism 126 may include a stored energy source 127 which advances the drive element 124 without user assistance. The stored energy source 127 may include a resilient biasing member such as a spring, or a pressurized gas, or electronically powered motor and/or gearbox.

The autoinjector 100 includes a dispensing mechanism protection mechanism 140. The dispensing mechanism protection mechanism 140 typically has two functions. Firstly, the dispensing mechanism protection mechanism 140 can function to prevent access to the discharge nozzle 122 prior to and after injection. Secondly, the autoinjector 100 can function, such that when put into an activated state, e.g., the dispensing mechanism protection mechanism 140 is moved to an unlocked position, the dispensing mechanism 120 can be activated.

The protection mechanism 140 covers at least a part of the discharge nozzle 122 when the drug holder 110 is in its retracted position proximally within the housing 130. This is to impede contact between the discharge nozzle 122 and a user. Alternatively, or in addition, the protection mechanism 140 is itself configured to retract proximally to expose the discharge nozzle 122 so that it can be brought into contact with a patient. The protection mechanism 140 includes a shield member 141 and return spring 142. The return spring 142 acts to extend the shield member 141 from the housing 130, thereby covering the discharge nozzle 122 when no force is applied to the distal end of the protection mechanism 140. If a user applies a force to the shield member 141 against the action of the return spring 142 to overcome the bias of the return spring 142 (or a robotic surgical system causes such a force to be provided to the shield member 141), the shield member 141 retracts within the housing 130, thereby exposing the discharge nozzle 122. The protection mechanism 140 may alternatively, or in addition, include an extension mechanism (not shown) for extending the discharge nozzle 122 beyond the housing 130, and may further include a retracting mechanism (not shown) for retracting the discharge nozzle 122 within the housing 130. The protection mechanism 140 may alternatively, or in addition, include a housing cap and/or discharge nozzle boot, which can be attached to the autoinjector 100. Removal of the housing cap would typically also remove the discharge nozzle boot from the discharge nozzle 122.

The autoinjector 100 also includes a trigger 150. The trigger 150 includes a trigger button 151 which is located on an external surface of the housing 130 so that it is accessible by a user of the autoinjector 100 and/or by a robotic surgical system configured to control actuation of the trigger 150. When the trigger 150 is pressed by a user (or a robotic surgical system causes the trigger 150 to be pressed), it acts to release the drive mechanism 126 so that, via the drive element 124, the drug is then driven out of the drug holder 110 via the discharge nozzle 122.

The trigger 150 can also cooperate with the shield member 141 in such a way that the trigger 150 is prevented from being activated until the shield member 141 has been retracted proximally sufficiently into the housing 130 into an unlocked position, for example by pushing a distal end of the shield member 141 against the skin of a patient. When this has been done, the trigger 150 becomes unlocked, and the autoinjector 100 is activated such that the trigger 150 can be depressed and the injection and/or drug delivery sequence is then initiated. Alternatively, retraction of the shield member 141 alone in a proximal direction into the housing 130 can act to activate the drive mechanism 126 and initiate the injection and/or drug delivery sequence. In this way, the autoinjector 100 has device operation prevention mechanism which prevents dispensing of the drug by, for example, preventing accidental release of the dispensing mechanism 120 and/or accidental actuation of the trigger 150.

While the foregoing description relates to one example of an autoinjector, this example is presented purely for illustration, the present invention is not limited solely to such an autoinjector. A person skilled in the art understands that various modifications to the described autoinjector can be implemented within the scope of the present disclosure.

Autoinjectors of the present disclosure can be used to administer any of a variety of drugs, such as any of epinephrine, Rebif, Enbrel, Aranesp, atropine, pralidoxime chloride, and diazepam.

Infusion Pumps

Patients can require precise, continuous delivery of medication or medication delivery on a regular or frequent basis at set periodic intervals. Infusion pumps can provide such controlled drug infusion by facilitating the administering of the drug at a precise rate that keeps the drug concentration within a therapeutic margin, without requiring frequent attention by a healthcare professional or the patient.

Figure 2:
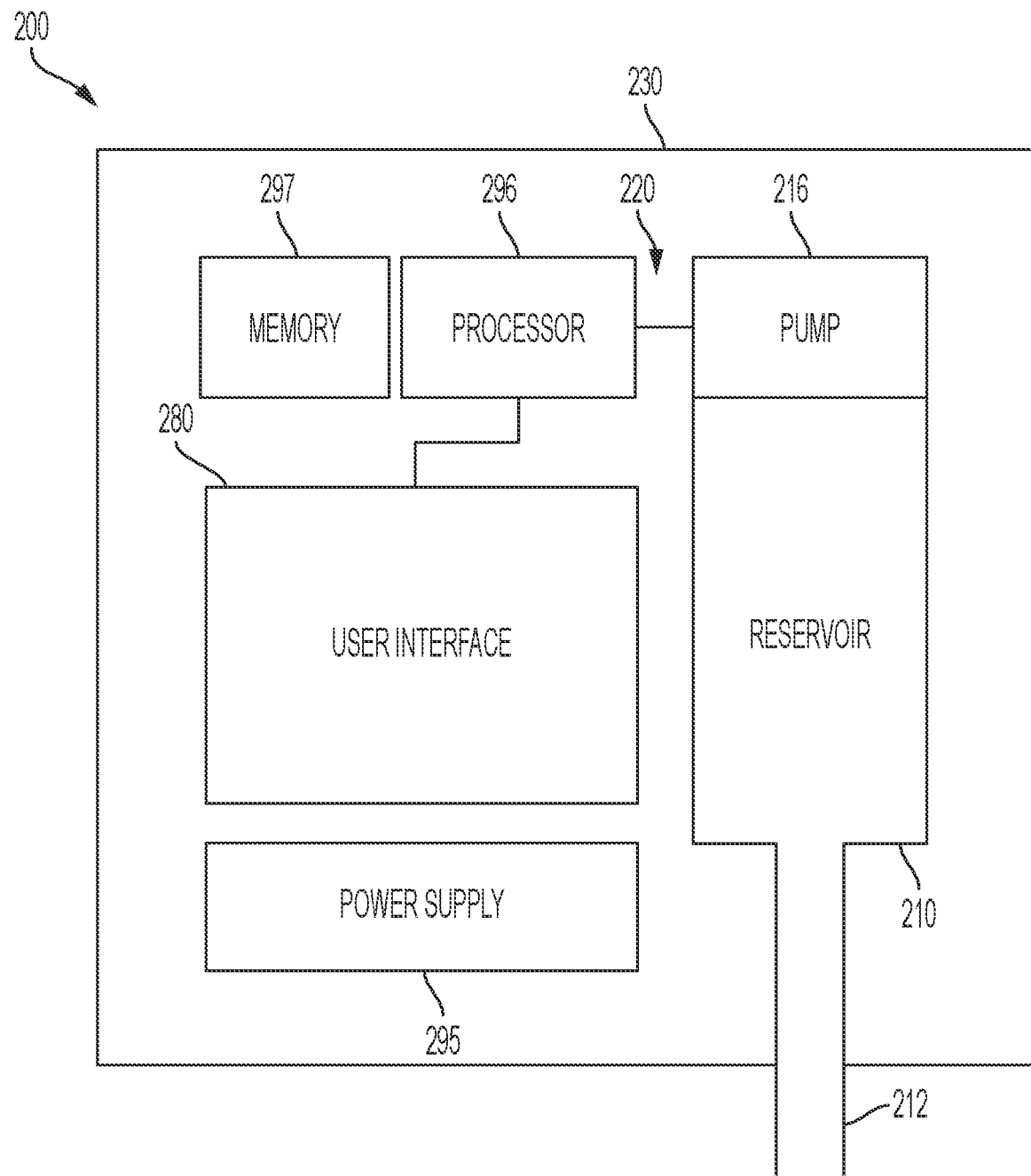
FIG. 2 is a schematic view of one embodiment of a second type of drug administration device, namely an infusion pump.

FIG. 2 is a schematic exemplary view of a second type of drug delivery device, namely an infusion pump 200, useable with the embodiments described herein. The infusion pump 200 includes a drug holder 210 (also referred to herein as a "reservoir") in the form of a reservoir for containing a drug to be delivered, and a dispensing mechanism 220 including a pump 216 configured to dispense a drug contained in the reservoir, so that the drug can be delivered to a patient. These components of the infusion pump 200 are located within a housing 230. The dispensing mechanism 220 further includes an infusion line 212. The drug is delivered from the reservoir 210 upon actuation of the pump 216 via the infusion line 212, which can take the form of a cannula. The pump 216 can take the form of an elastomeric pump, a peristaltic pump, an osmotic pump, or a motor-controlled piston in a syringe. Typically, the drug is delivered intravenously, although subcutaneous, arterial and epidural infusions can also be used.

Infusion pumps of the present disclosure can be used to administer any of a variety of drugs, such as any of insulin, antropine sulfate, avibactam sodium, bendamustine hydrochloride, carboplatin, daptomycin, epinephrine, levetiracetam, oxaliplatin, paclitaxel, pantoprazole sodium, treprostinil, vasopressin, voriconazole, and zoledronic acid.

The infusion pump 200 further includes control circuitry, for example a processor 296 in addition to a memory 297 and a user interface 280, which together provide a triggering mechanism and/or dosage selector for the pump 200. The user interface 280 can be implemented by a display screen located on the housing 230 of the infusion pump 200. The control circuitry and user interface 280 can be located within the housing 230 or external thereto and can communicate via a wired or wireless interface with the pump 216 to control its operation.

Actuation of the pump 216 is controlled by the processor 296, which is in communication with the pump 216 for controlling the pump's operation. The processor 296 can be programmed by a user (e.g., patient or healthcare professional) via a user interface 280 and/or can be programmed electronically using a computer system (e.g., using a robotic surgical system configured to control operation of the pump 216). This enables the infusion pump 200 to deliver the drug to a patient in a controlled manner. The user (or computer system) can enter parameters, such as infusion duration and delivery rate. The delivery rate can be set to a constant infusion rate or as set intervals for periodic delivery, typically within pre-programmed limits. The programmed parameters for controlling the pump 216 are stored in and retrieved from the memory 297 which is in communication with the processor 296. The user interface 280 can take the form of a touch screen or a keypad.

A power supply 295 provides power to the pump 216 and can take the form of an energy source which is integral to the pump 216 and/or a mechanism for connecting the pump 216 to an external source of power.

The infusion pump 200 can take on a variety of different physical forms depending on its designated use. It can be a stationary, non-portable device, e.g., for use at a patient's bedside, in an operating room, etc., or it can be an ambulatory infusion pump which is designed to be portable or wearable. An integral power supply 295 is particularly beneficial for ambulatory infusion pumps.

While the foregoing description relates to one example of an infusion pump, this example is provided purely for illustration. The present disclosure is not limited to such an infusion pump. A person skilled in the art understands that various modifications to the described infusion pump can be implemented within the scope of the present disclosure. For example, the processor may be pre-programmed, such that it is not necessary for the infusion pump to include a user interface.

Inhalers

Figure 3:
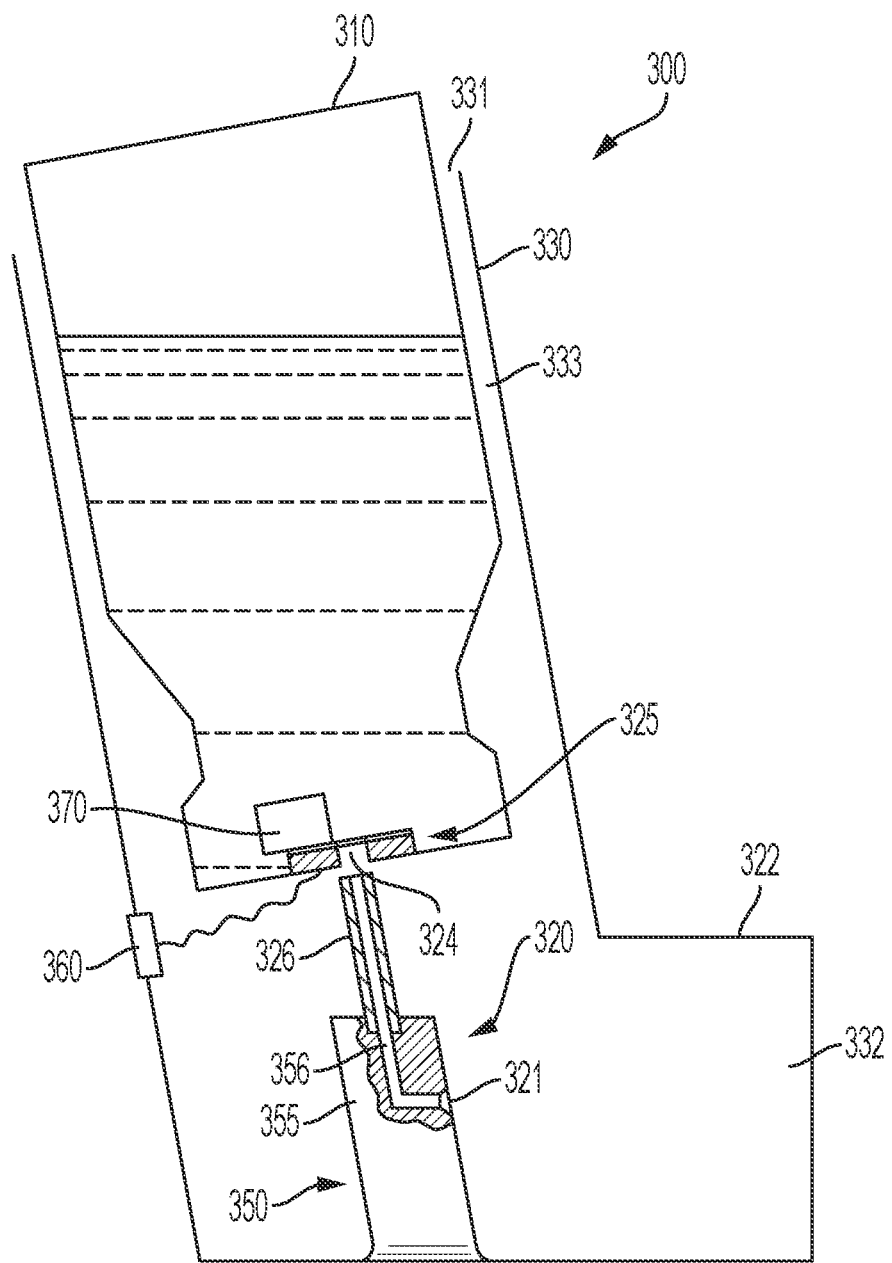
FIG. 3 is a schematic view of one embodiment of a third type of drug administration device, namely an inhaler.

FIG. 3 is a schematic view of a third type of drug administration device, namely an inhaler 300. Inhaler 300 includes a drug holder 310 in the form of a canister. The drug holder 310 contains a drug that would typically be in solution or suspension with a suitable carrier liquid. The inhaler 300 further includes a dispensing mechanism 320, which includes a pressurized gas for pressurizing the drug holder 310, a valve 325 and nozzle 321. The valve 325 forms an outlet of the drug holder 310. The valve 325 includes a narrow opening 324 formed in the drug holder 310 and a movable element 326 that controls the opening 324. When the movable element 326 is in a resting position, the valve 325 is in a closed or unactuated state in which the opening 324 is closed and the drug holder 310 is sealed. When the movable element 326 is actuated from the resting position to an actuated position, the valve 325 is actuated into an open state in which the opening 324 is open. Actuation of the movable element 326 from the resting position to the actuated position comprises moving the movable element 326 into the drug holder 310. The movable element 326 is resiliently biased into the resting position. In the open state of the valve 325, the pressurized gas propels the drug in solution or suspension with the suitable liquid out of the drug holder 310 through the opening 324 at high speed. The high speed passage of the liquid through the narrow opening 324 causes the liquid to be atomized, that is, to transform from a bulk liquid into a mist of fine droplets of liquid and/or into a gas cloud. A patient may inhale the mist of fine droplets and/or the gas cloud into a respiratory passage. Hence, the inhaler 300 is capable of delivering a drug retained within the drug holder 310 into a respiratory passage of a patient.

The drug holder 310 is removably held within a housing 330 of the inhaler 300. A passage 333 formed in the housing 330 connects a first opening 331 in the housing 330 and a second opening 332 in the housing 330. The drug holder 310 is received within the passage 333. The drug holder 310 is slidably insertable through the first opening 331 of the housing 330 into the passage 333. The second opening 332 of the housing 330 forms a mouthpiece 322 configured to be placed in a patient's mouth or a nosepiece configured to be placed in a patient's nostril, or a mask configured to be placed over the patient's mouth and nose. The drug holder 310, the first opening 331 and the passage 333 are sized such that air can flow through the passage 333, around the drug holder 310, between the first opening 331 and the second opening 332. The inhaler 300 can be provided with a dispensing mechanism protection mechanism 140 in the form of a cap (not shown) which can be fitted to the mouthpiece 322.

Inhaler 300 further includes a trigger 350 including a valve actuation feature 355 configured to actuate the valve 325 when the trigger 350 is activated. The valve actuation feature 355 is a projection of the housing 330 into the passage 333. The drug holder 310 is slidably movable within the passage 333 from a first position into a second position. In the first position, an end of the movable element 326 in the resting position abuts the valve actuation feature 355. In the second position, the drug holder 310 can be displaced towards the valve actuation feature 355 such that the valve actuation feature 355 moves the movable element 326 into the drug holder 310 to actuate the valve 325 into the open state. The user's hand (or other element handheld by a user or controlled by a robotic surgical system) provides the necessary force to move the drug holder 310 from the first position to the second position against the resiliently biased movable element 326. The valve actuation feature 355 includes an inlet 356, which is connected to the nozzle 321. The inlet 356 of the valve actuation feature 355 is sized and positioned to couple to the opening 324 of the valve 325 such that the ejected mist of droplets and/or gas cloud can enter the inlet 356 and exit from the nozzle 321 into the passage 333. The nozzle 321 assists in the atomization of the bulk liquid into the mist of droplets and/or gas cloud.

The valve 325 provides a metering mechanism 370. The metering mechanism 370 is configured to close the valve after a measured amount of liquid, and therefore, drug, has passed through the opening 324. This allows a controlled dose to be administered to the patient. Typically, the measured amount of liquid is pre-set, however, the inhaler 300 can be equipped with a dosage selector 360 that is operable by a user and/or electronically by a computer system to change the defined amount of liquid.

While the foregoing description relates to one particular example of an inhaler, this example is purely illustrative. The description should not be seen as limited only to such an inhaler. A person skilled in the art understands that numerous other types of inhalers and nebulizers may be used with the present disclosure. For example, the drug can be in a powdered form, the drug can be in liquid form, or the drug can be atomized by other forms of dispensing mechanism 320 including ultrasonic vibration, compressed gas, a vibrating mesh, or a heat source.

The inhalers of the present disclosure can be used to administer any of a variety of drugs, such as any of mometasone, fluticasone, ciclesonide, budesonide, beclomethasone, vilanterol, salmeterol, formoterol, umeclidinium, glycopyrrolate, tiotropium, aclidinium, indacaterol, salmeterol, and olodaterol.

Drug Administration Devices

As will be appreciated from the foregoing, various components of drug delivery devices are common to all such devices. These components form the essential components of a universal drug administration device. A drug administration device delivers a drug to a patient, where the drug is provided in a defined dosage form within the drug administration device.

Figure 4:
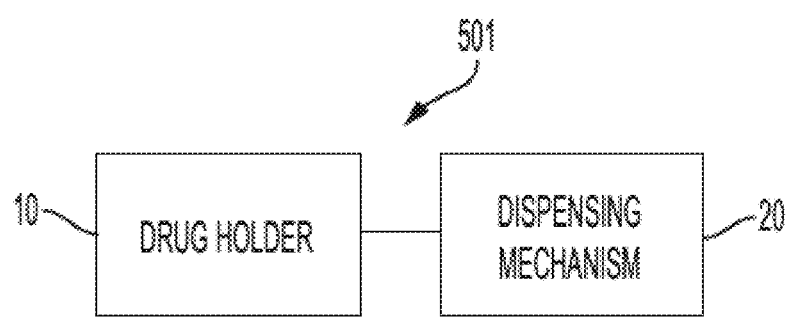
FIG. 4 is a schematic view of a general drug administration device.
Figure 5:
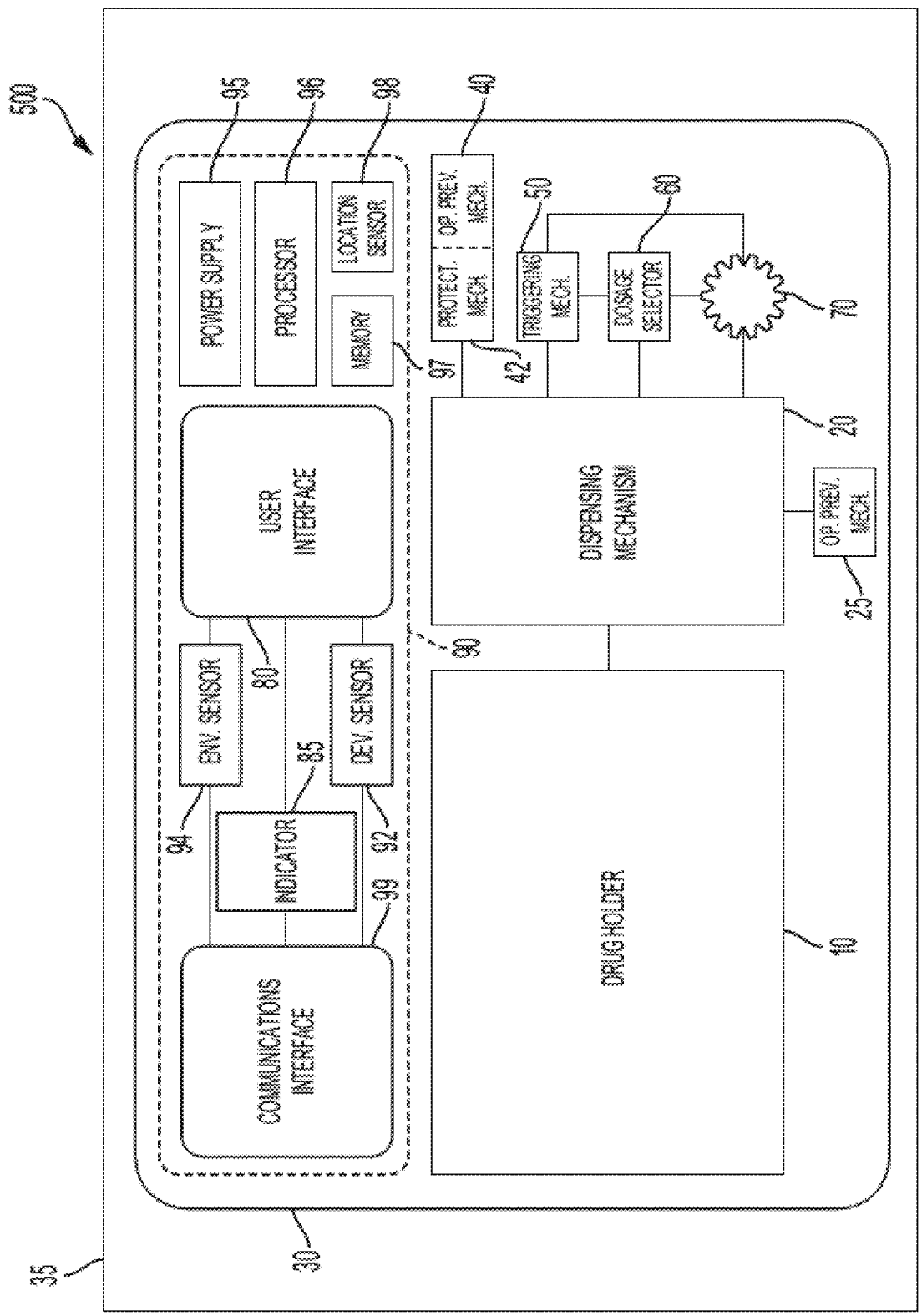
FIG. 5 is a schematic view of a universal drug administration device.

FIG. 4 is a generalized schematic view of such a universal drug administration device 501, and FIG. 5 is an exemplary embodiment of such a universal drug administration device 500. Examples of the universal drug administration device 500 include injection devices (e.g., autoinjectors, jet injectors, and infusion pumps), nasal spray devices, and inhalers.

As shown in FIG. 4, the drug administration device 501 includes in general form the features of a drug holder 10 and a dispensing mechanism 20. The drug holder 10 holds a drug in a dosage form to be administered. The dispensing mechanism 20 is configured to release the dosage form from the drug holder 10 so that the drug can be administered to a patient.

FIG. 5 shows a further universal drug administration device 500 which includes a number of additional features. A person skilled in the art understands that these additional features are optional for different embodiments and can be utilized in a variety of different combinations such that the additional features may be present or may be omitted from a given embodiment of a particular drug administration device, depending upon requirements, such as the type of drug, dosage form of the drug, medical indication being treated with the drug, safety requirements, whether the device is powered, whether the device is portable, whether the device is used for self-administration, and many other requirements which will be appreciated by a person skilled in the art. Similar to the universal device of FIG. 4, the drug administration device 500 of FIG. 5 includes a housing 30 which accommodates the drug holder 10 and dispensing mechanism 20.

The device 500 is provided with a triggering mechanism 50 for initiating the release of the drug from the drug holder 10 by the dispensing mechanism 20. The device 500 includes the feature of a metering/dosing mechanism 70 which measures out a set dose to be released from the drug holder 10 via the dispensing mechanism 20. In this manner, the drug administration device 500 can provide a known dose of determined size. The device 500 includes a dosage selector 60 which enables a user to set the dose volume of drug to be measured out by the metering mechanism 50. The dose volume can be set to one specific value of a plurality of predefined discrete dose volumes, or any value of predefined dose volume within a range of dose volumes.

The device 500 includes a device operation prevention mechanism 40 or 25 which when in a locked state will prevent and/or stop the dispensing mechanism 20 from releasing the drug out of the drug holder 10, and when in an unlocked state will permit the dispensing mechanism 20 to release the drug dosage from out of the drug holder 10. This can prevent accidental administration of the drug, for example to prevent dosing at an incorrect time, or for preventing inadvertent actuation. The device 500 also includes a dispensing mechanism protection mechanism 42 which prevents access to at least a part of the dispensing mechanism 20, for example for safety reasons. The device operation prevention mechanism 40 and the dispensing mechanism protection mechanism 42 can be the same component.

The device 500 includes a device indicator 85 which is configured to present information about the status of the drug administration device and/or the drug contained therein. The device indicator 85 can be a visual indicator, such as a display screen, or an audio indicator. The device 500 includes a user interface 80 which can be configured to present a user of the device 500 with information about the device 500 and/or to enable the user to control the device 500. The device 500 includes a device sensor 92 which is configured to sense information relating to the drug administration device and/or the drug contained therein, for example dosage form and device parameters. As an example, in embodiments which include a metering mechanism 70 and a dosage selector 60, the embodiment can further include one or more device sensors 92 configured to sense one or more of: the dose selected by a user using dosage selector 60, the dose metered by the metering mechanism 70 and the dose dispensed by the dispensing mechanism 20. Similarly, an environment sensor 94 is provided which is configured to sense information relating to the environment in which the device 500 is present, such as the temperature of the environment, the humidity of the environment, location, and time. There can be a dedicated location sensor 98 which is configured to determine the geographical location of the device 500, e.g., via satellite position determination, such as GPS. The device 500 also includes a communications interface 99 which can communicate externally data which has been acquired from the various sensors about the device and/or drug.

If required, the device 500 includes a power supply 95 for delivering electrical power to one or more electrical components of the device 500. The power supply 95 can be a source of power which is integral to device 500 and/or a mechanism for connecting device 500 to an external source of power. The drug administration device 500 also includes a computer system 90 including a processor 96 and a memory 97 powered by the power supply 95 and in communication with each other, and optionally with other electrical and control components of the device 500, such as the environment sensor 94, the location sensor 98, the device sensor 92, the communications interface 99, and/or the indicator 85. The processor 96 is configured to obtain data acquired from the environment sensor 94, the device sensor 92, the communications interface 99, the location sensor 98, and/or the user interface 80 and process it to provide data output, for example to indicator 85 and/or to communications interface 99.

In some embodiments, the drug administration device 500 is enclosed in packaging 35. The packaging 35 can further include a combination of a processor 96, a memory 97, a user interface 80, a device indicator 85, a device sensor 92, a location sensor 98, and/or environment sensors 94 as described herein, and these can be located externally on the housing of the device 500.

A person skilled in the art will appreciate that the universal drug administration device 500 including the drug holder 10 and the dispensing mechanism 20 can be provided with a variety of the optional features described above, in a number of different combinations. Moreover, the drug administration device 500 can include more than one drug holder 10, optionally with more than one dispensing mechanism 20, such that each drug holder 10 has its own associated dispensing mechanism 20.

Drug Dosage Forms

Conventionally, drug administration devices utilize a liquid dosage form. It will be appreciated by a person skilled in the art, however, that other dosage forms are available.

One such common dosage form is a tablet. The tablet may be formed from a combination of the drug and an excipient that are compressed together. Other dosage forms are pastes, creams, powders, ear drops, and eye drops.

Further examples of drug dosage forms include dermal patches, drug eluting stents and intrauterine devices. In these examples, the body of the device includes the drug and can be configured to allow the release of the drug under certain circumstances. For example, a dermal patch may include a polymeric composition containing the drug. The polymeric composition allows the drug to diffuse out of the polymeric composition and into skin of a patient. Drug eluting stents and intrauterine devices can operate in an analogous manner. In this way, the patches, stents, and intrauterine devices can themselves be considered drug holders with an associated dispensing mechanism.

Any of these dosage forms can be configured to have the drug release initiated by certain conditions. This can allow the drug to be released at a desired time or location after the dosage form has been introduced into the patient. In particular, the drug release can be initiated by an external stimulus. Moreover, these dosage forms can be contained prior to administration in a housing, which can be in the form of packaging. This housing can contain some of the optional features described above which are utilized with the universal drug administration device 500.

The drug administered by the drug administration devices of the present disclosure can be any substance that causes a change in an organism's physiology or psychology when consumed. Examples of drugs that the drug administration devices of the present disclosure can administer include 5-alpha-reductase inhibitors, 5-aminosalicylates, 5HT3 receptor antagonists, ACE inhibitors with calcium channel blocking agents, ACE inhibitors with thiazides, adamantane antivirals, adrenal cortical steroids, adrenal corticosteroid inhibitors, adrenergic bronchodilators, agents for hypertensive emergencies, agents for pulmonary hypertension, aldosterone receptor antagonists, alkylating agents, allergenics, alpha-glucosidase inhibitors, alternative medicines, amebicides, aminoglycosides, aminopenicillins, aminosalicylates, AMPA receptor antagonists, amylin analogs, analgesic combinations, analgesics, androgens and anabolic steroids, Angiotensin Converting Enzyme Inhibitors, angiotensin II inhibitors with calcium channel blockers, angiotensin II inhibitors with thiazides, angiotensin receptor blockers, angiotensin receptor blockers and neprilysin inhibitors, anorectal preparations, anorexiants, antacids, anthelmintics, anti-angiogenic ophthalmic agents, anti-CTLA-4 monoclonal antibodies, anti-infectives, anti-PD-1 monoclonal antibodies, antiadrenergic agents (central) with thiazides, antiadrenergic agents (peripheral) with thiazides, antiadrenergic agents, centrally acting, antiadrenergic agents, peripherally acting, antiandrogens, antianginal agents, antiarrhythmic agents, antiasthmatic combinations, antibiotics/antineoplastics, anticholinergic antiemetics, anticholinergic antiparkinson agents, anticholinergic bronchodilators, anticholinergic chronotropic agents, anticholinergics/antispasmodics, anticoagulant reversal agents, anticoagulants, anticonvulsants, antidepressants, antidiabetic agents, antidiabetic combinations, antidiarrheals, antidiuretic hormones, antidotes, antiemetic/antivertigo agents, antifungals, antigonadotropic agents, antigout agents, antihistamines, antihyperlipidemic agents, antihyperlipidemic combinations, antihypertensive combinations, antihyperuricemic agents, antimalarial agents, antimalarial combinations, antimalarial quinolones, antimanic agents, antimetabolites, antimigraine agents, antineoplastic combinations, antineoplastic detoxifying agents, antineoplastic interferons, antineoplastics, antiparkinson agents, antiplatelet agents, antipseudomonal penicillins, antipsoriatics, antipsychotics, antirheumatics, antiseptic and germicides, antithyroid agents, antitoxins and antivenins, antituberculosis agents, antituberculosis combinations, antitussives, antiviral agents, antiviral boosters, antiviral combinations, antiviral interferons, anxiolytics, sedatives, and hypnotics, aromatase inhibitors, atypical antipsychotics, azole antifungals, bacterial vaccines, barbiturate anticonvulsants, barbiturates, BCR-ABL tyrosine kinase inhibitors, benzodiazepine anticonvulsants, benzodiazepines, beta blockers with calcium channel blockers, beta blockers with thiazides, beta-adrenergic blocking agents, beta-lactamase inhibitors, bile acid sequestrants, biologicals, bisphosphonates, bone morphogenetic proteins, bone resorption inhibitors, bronchodilator combinations, bronchodilators, calcimimetics, calcineurin inhibitors, calcitonin, calcium channel blocking agents, carbamate anticonvulsants, carbapenems, carbapenems/beta-lactamase inhibitors, carbonic anhydrase inhibitor anticonvulsants, carbonic anhydrase inhibitors, cardiac stressing agents, cardioselective beta blockers, cardiovascular agents, catecholamines, cation exchange resins, CD20 monoclonal antibodies, CD30 monoclonal antibodies, CD33 monoclonal antibodies, CD38 monoclonal antibodies, CD52 monoclonal antibodies, CDK 4/6 inhibitors, central nervous system agents, cephalosporins, cephalosporins/beta-lactamase inhibitors, cerumenolytics, CFTR combinations, CFTR potentiators, CGRP inhibitors, chelating agents, chemokine receptor antagonist, chloride channel activators, cholesterol absorption inhibitors, cholinergic agonists, cholinergic muscle stimulants, cholinesterase inhibitors, CNS stimulants, coagulation modifiers, colony stimulating factors, contraceptives, corticotropin, coumarins and indandiones, cox-2 inhibitors, decongestants, dermatological agents, diagnostic radiopharmaceuticals, diarylquinolines, dibenzazepine anticonvulsants, digestive enzymes, dipeptidyl peptidase 4 inhibitors, diuretics, dopaminergic antiparkinsonism agents, drugs used in alcohol dependence, echinocandins, EGFR inhibitors, estrogen receptor antagonists, estrogens, expectorants, factor Xa inhibitors, fatty acid derivative anticonvulsants, fibric acid derivatives, first generation cephalosporins, fourth generation cephalosporins, functional bowel disorder agents, gallstone solubilizing agents, gamma-aminobutyric acid analogs, gamma-aminobutyric acid reuptake inhibitors, gastrointestinal agents, general anesthetics, genitourinary tract agents, GI stimulants, glucocorticoids, glucose elevating agents, glycopeptide antibiotics, glycoprotein platelet inhibitors, glycylcyclines, gonadotropin releasing hormones, gonadotropin-releasing hormone antagonists, gonadotropins, group I antiarrhythmics, group II antiarrhythmics, group III antiarrhythmics, group IV antiarrhythmics, group V antiarrhythmics, growth hormone receptor blockers, growth hormones, guanylate cyclase-C agonists, *H. pylori* eradication agents, H2 antagonists, hedgehog pathway inhibitors, hematopoietic stem cell mobilizer, heparin antagonists, heparins, HER2 inhibitors, herbal products, histone deacetylase inhibitors, hormones, hormones/antineoplastics, hydantoin anticonvulsants, hydrazide derivatives, illicit (street) drugs, immune globulins, immunologic agents, immunostimulants, immunosuppressive agents, impotence agents, in vivo diagnostic biologicals, incretin mimetics, inhaled anti-infectives, inhaled corticosteroids, inotropic agents, insulin, insulin-like growth factors, integrase strand transfer inhibitor, interferons, interleukin inhibitors, interleukins, intravenous nutritional products, iodinated contrast media, ionic iodinated contrast media, iron products, ketolides, laxatives, leprostatics, leukotriene modifiers, lincomycin derivatives, local injectable anesthetics, local injectable anesthetics with corticosteroids, loop diuretics, lung surfactants, lymphatic staining agents, lysosomal enzymes, macrolide derivatives, macrolides, magnetic resonance imaging contrast media, mast cell stabilizers, medical gas, meglitinides, metabolic agents, methylxanthines, mineralocorticoids, minerals and electrolytes, miscellaneous agents, miscellaneous analgesics, miscellaneous antibiotics, miscellaneous anticonvulsants, miscellaneous antidepressants, miscellaneous antidiabetic agents, miscellaneous antiemetics, miscellaneous antifungals, miscellaneous antihyperlipidemic agents, miscellaneous antihypertensive combinations, miscellaneous antimalarials, miscellaneous antineoplastics, miscellaneous antiparkinson agents, miscellaneous antipsychotic agents, miscellaneous antituberculosis agents, miscellaneous antivirals, miscellaneous anxiolytics, sedatives and hypnotics, miscellaneous bone resorption inhibitors, miscellaneous cardiovascular agents, miscellaneous central nervous system agents, miscellaneous coagulation modifiers, miscellaneous diagnostic dyes, miscellaneous diuretics, miscellaneous genitourinary tract agents, miscellaneous GI agents, miscellaneous hormones, miscellaneous metabolic agents, miscellaneous ophthalmic agents, miscellaneous otic agents, miscellaneous respiratory agents, miscellaneous sex hormones, miscellaneous topical agents, miscellaneous uncategorized agents, miscellaneous vaginal agents, mitotic inhibitors, monoamine oxidase inhibitors, mouth and throat products, mTOR inhibitors, mucolytics, multikinase inhibitors, muscle relaxants, mydriatics, narcotic analgesic combinations, narcotic analgesics, nasal anti-infectives, nasal antihistamines and decongestants, nasal lubricants and irrigations, nasal preparations, nasal steroids, natural penicillins, neprilysin inhibitors, neuraminidase inhibitors, neuromuscular blocking agents, neuronal potassium channel openers, next generation cephalosporins, nicotinic acid derivatives, NK1 receptor antagonists, NNRTIs, non-cardioselective beta blockers, non-iodinated contrast media, non-ionic iodinated contrast media, non-sulfonylureas, Nonsteroidal anti-inflammatory drugs, NS5A inhibitors, nucleoside reverse transcriptase inhibitors (NRTIs), nutraceutical products, nutritional products, ophthalmic anesthetics, ophthalmic anti-infectives, ophthalmic anti-inflammatory agents, ophthalmic antihistamines and decongestants, ophthalmic diagnostic agents, ophthalmic glaucoma agents, ophthalmic lubricants and irrigations, ophthalmic preparations, ophthalmic steroids, ophthalmic steroids with anti-infectives, ophthalmic surgical agents, oral nutritional supplements, other immunostimulants, other immunosuppressants, otic anesthetics, otic anti-infectives, otic preparations, otic steroids, otic steroids with anti-infectives, oxazolidinedione anticonvulsants, oxazolidinone antibiotics, parathyroid hormone and analogs, PARP inhibitors, PCSK9 inhibitors, penicillinase resistant penicillins, penicillins, peripheral opioid receptor antagonists, peripheral opioid receptor mixed agonists/antagonists, peripheral vasodilators, peripherally acting antiobesity agents, phenothiazine antiemetics, phenothiazine antipsychotics, phenylpiperazine antidepressants, phosphate binders, PI3K inhibitors, plasma expanders, platelet aggregation inhibitors, platelet-stimulating agents, polyenes, potassium sparing diuretics with thiazides, potassium-sparing diuretics, probiotics, progesterone receptor modulators, progestins, prolactin inhibitors, prostaglandin D2 antagonists, protease inhibitors, protease-activated receptor-1 antagonists, proteasome inhibitors, proton pump inhibitors, psoralens, psychotherapeutic agents, psychotherapeutic combinations, purine nucleosides, pyrrolidine anticonvulsants, quinolones, radiocontrast agents, radiologic adjuncts, radiologic agents, radiologic conjugating agents, radiopharmaceuticals, recombinant human erythropoietins, renin inhibitors, respiratory agents, respiratory inhalant products, rifamycin derivatives, salicylates, sclerosing agents, second generation cephalosporins, selective estrogen receptor modulators, selective immunosuppressants, selective phosphodiesterase-4 inhibitors, selective serotonin reuptake inhibitors, serotonin-norepinephrine reuptake inhibitors, serotoninergic neuroenteric modulators, sex hormone combinations, sex hormones, SGLT-2 inhibitors, skeletal muscle relaxant combinations, skeletal muscle relaxants, smoking cessation agents, somatostatin and somatostatin analogs, spermicides, statins, sterile irrigating solutions, streptogramins, streptomyces derivatives, succinimide anticonvulsants, sulfonamides, sulfonylureas, synthetic ovulation stimulants, tetracyclic antidepressants, tetracyclines, therapeutic radiopharmaceuticals, therapeutic vaccines, thiazide diuretics, thiazolidinediones, thioxanthenes, third generation cephalosporins, thrombin inhibitors, thrombolytics, thyroid drugs, TNF alfa inhibitors, tocolytic agents, topical acne agents, topical agents, topical allergy diagnostic agents, topical anesthetics, topical anti-infectives, topical anti-rosacea agents, topical antibiotics, topical antifungals, topical antihistamines, topical antineoplastics, topical antipsoriatics, topical antivirals, topical astringents, topical debriding agents, topical depigmenting agents, topical emollients, topical keratolytics, topical non-steroidal anti-inflammatories, topical photochemotherapeutics, topical rubefacient, topical steroids, topical steroids with anti-infectives, transthyretin stabilizers, triazine anticonvulsants, tricyclic antidepressants, trifunctional monoclonal antibodies, ultrasound contrast media, upper respiratory combinations, urea anticonvulsants, urea cycle disorder agents, urinary anti-infectives, urinary antispasmodics, urinary pH modifiers, uterotonic agents, vaccine combinations, vaginal anti-infectives, vaginal preparations, vasodilators, vasopressin antagonists, vasopressors, VEGF/VEGFR inhibitors, viral vaccines, viscosupplementation agents, vitamin and mineral combinations, vitamins, or VMAT2 inhibitors. The drug administration devices of the present disclosure may administer a drug selected from epinephrine, Rebif, Enbrel, Aranesp, atropine, pralidoxime chloride, diazepam, insulin, antropine sulfate, avibactam sodium, bendamustine hydrochloride, carboplatin, daptomycin, epinephrine, levetiracetam, oxaliplatin, paclitaxel, pantoprazole sodium, treprostinil, vasopressin, voriconazole, zoledronic acid, mometasone, fluticasone, ciclesonide, budesonide, beclomethasone, vilanterol, salmeterol, formoterol, umeclidinium, glycopyrrolate, tiotropium, aclidinium, indacaterol, salmeterol, and olodaterol.

As mentioned above, any of a variety of drugs can be delivered using a drug administration device.

Drug Housings

As described above, a dosage form can be provided in a holder that is appropriate for the particular dosage form being utilized. For example, a drug in a liquid dosage form can be held prior to administration within a holder in the form of a vial with a stopper, or a syringe with a plunger. A drug in solid or powder dosage form, e.g., as tablets, can be contained in a housing which is arranged to hold the tablets securely prior to administration.

The housing can include one or a plurality of drug holders, where each holder contains a dosage form, e.g., the drug can be in a tablet dosage form and the housing can be in the form of a blister pack, where a tablet is held within each of a plurality of holders. The holders being in the form of recesses in the blister pack.

Figure 6:
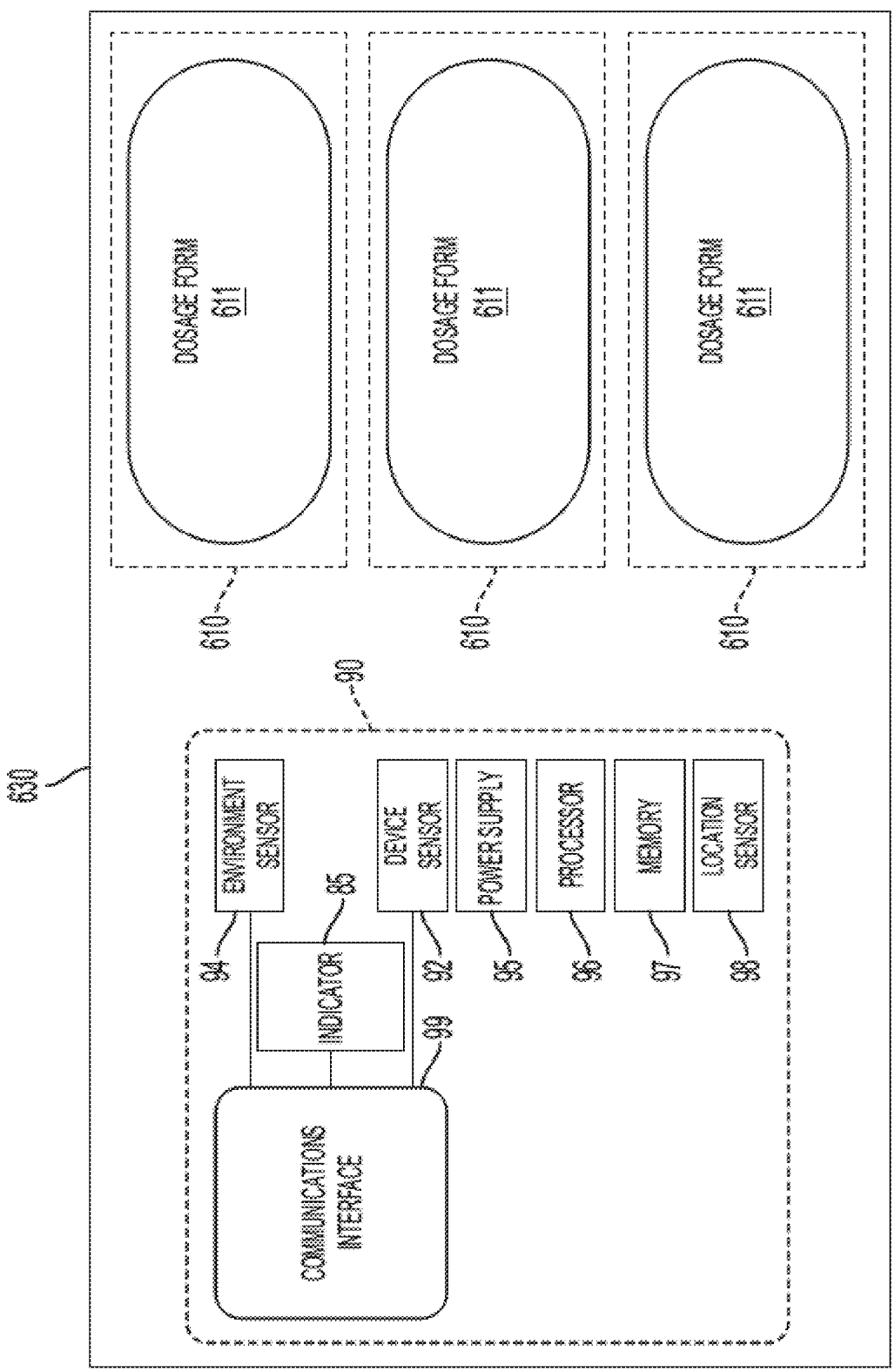
FIG. 6 is a schematic view of one embodiment of a housing for a dosage form.

FIG. 6 depicts a housing 630 that includes a plurality of drug holders 610 that each contain a dosage form 611. The housing 630 can have at least one environment sensor 94, which is configured to sense information relating to the environment in which the housing 630 is present, such as the temperature of the environment, time or location. The housing 630 can include at least one device sensor 92, which is configured to sense information relating to the drug of the dosage form 611 contained within the holder 610. There can be a dedicated location sensor 98 which is configured to determine the geographical location of the housing 630, e.g., via satellite position determination, such as GPS.

The housing 630 can include an indicator 85 which is configured to present information about the status of the drug of the dosage form 611 contained within the holder 610 to a user of the drug housing. The housing 630 can also include a communications interface 99 which can communicate information externally via a wired or wireless transfer of data pertaining to the drug housing 630, environment, time, or location and/or the drug itself.

If required, the housing 630 can include a power supply 95 for delivering electrical power to one or more electrical components of the housing 630. The power supply 95 can be a source of power which is integral to housing 630 and/or a mechanism for connecting the housing 630 to an external source of power. The housing 630 can also include a computer system 90 including a processor 96 and a memory 97 powered by the power supply 95 and in communication with each other, and optionally with other electrical and control components of the housing 630, such as the environment sensor 94, the location sensor 98, the device sensor 92, the communications interface 99, and/or the indicator 85. The processor 96 is configured to obtain data acquired from the environment sensor 94, the device sensor 92, the communications interface 99, the location sensor 98, and/or the user interface 80 and process it to provide data output, for example to the indicator 85 and/or to the communications interface 99.

The housing 630 can be in the form of packaging. Alternatively, additional packaging can be present to contain and surround the housing 630.

The holder 610 or the additional packaging the themselves include one or more of the device sensor 92, the environment sensor 94, the indicator 85, the communications interface 99, the power supply 95, location sensor 98, and the computer system including the processor 96 and the memory 85, as described above.

Electronic Communication

Figure 7:
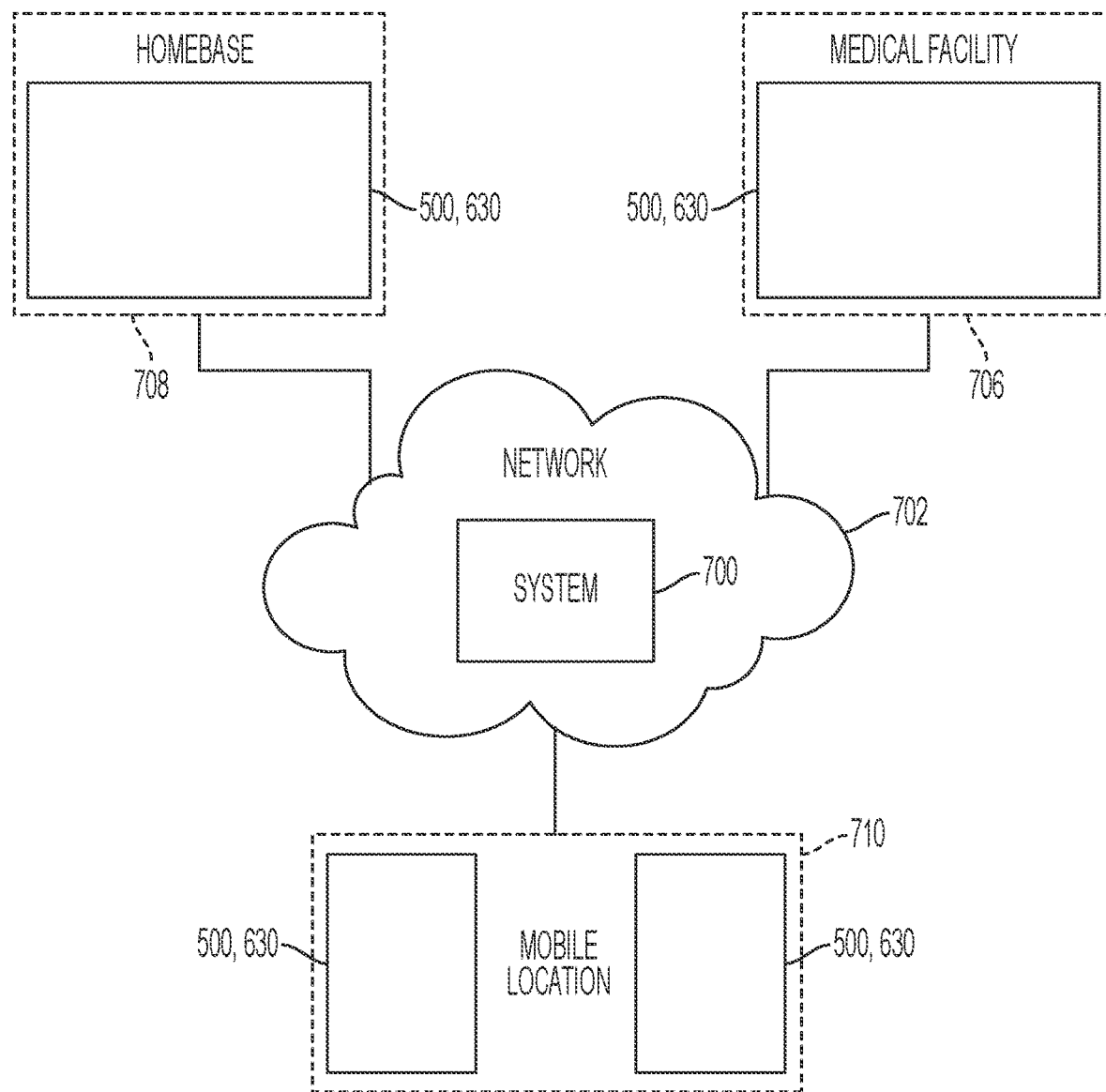
FIG. 7 is a schematic view of one embodiment of a communication network system with which the drug administration devices and housing can operate.

As mentioned above, the communications interface 99 can be associated with the drug administration device 500 or the drug housing 630, by being included within or on the housing 30, 630, or alternatively within or on the packaging 35. Such a communications interface 99 can be configured to communicate with a remote computer system, such as central computer system 700 shown in FIG. 7. As shown in FIG. 7, the communications interface 99 associated with the drug administration device 500 or the housing 630 is configured to communicate with a central computer system 700 through a communications network 702 from any number of locations such as a medical facility 706 (e.g., a hospital or other medical care center), a home base 708 (e.g., a patient's home or office or a care taker's home or office), or a mobile location 710. The communications interface 99 can be configured to access the system 700 through a wired and/or wireless connection to the network 702. In an exemplary embodiment, the communications interface 99 of FIG. 6 is configured to access the system 700 wirelessly, e.g., through Wi-Fi connection(s), which can facilitate accessibility of the system 700 from almost any location in the world.

A person skilled in the art will appreciate that the system 700 can include security features such that the aspects of the system 700 available to any particular user can be determined based on, e.g., the identity of the user and/or the location from which the user is accessing the system. To that end, each user can have a unique username, password, biometric data, and/or other security credentials to facilitate access to the system 700. The received security parameter information can be checked against a database of authorized users to determine whether the user is authorized and to what extent the user is permitted to interact with the system, view information stored in the system, and so forth.

Computer Systems

As discussed herein, one or more aspects or features of the subject matter described herein, for example components of the central computer system 700, the processor 96, the power supply 95, the memory 97, the communications interface 99, the user interface 80, the device indicators 85, the device sensors 92, the environment sensors 94, and the location sensors 98, can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system can include clients and servers. A client and server are generally remote from each other and typically interact through a communications network, e.g., the Internet, a wireless wide area network, a local area network, a wide area network, or a wired network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" as used herein refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein, for example the user interface 80 (which can be integrated or separate to the administration device 500 or the housing 630), can be implemented on a computer having a display screen, such as for example a cathode ray tube (CRT) or a liquid crystal display (LCD) or a light emitting diode (LED) monitor for displaying information to the user. The display screen can allow input thereto directly (e.g., as a touch screen) or indirectly (e.g., via an input device such as a keypad or voice recognition hardware and software). Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. As described above, this feedback may be provided via one or more device indicators 85 in addition to the user interface 80. The device indicators 85 can interact with one or more of the device sensor(s) 92, the environment sensor(s) 94, and/or the location sensor(s) 98 in order to provide this feedback, or to receive input from the user.

Figure 8:
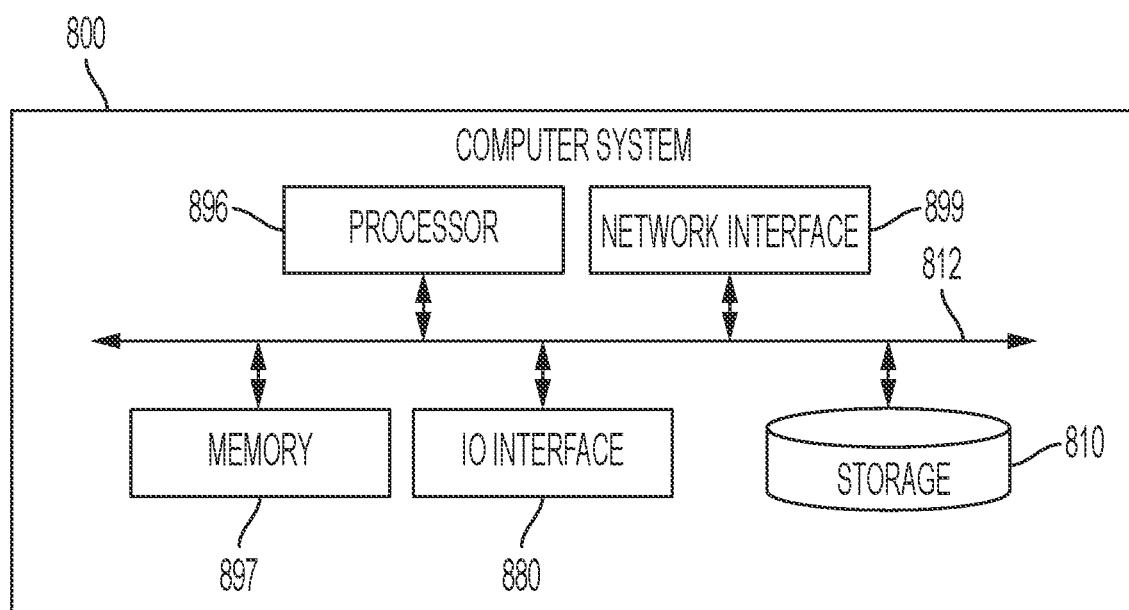
FIG. 8 is a schematic view of one embodiment of a computer system with which the drug administration devices and housing can operate.

FIG. 8 illustrates one exemplary embodiment of the computer system 700, depicted as computer system 800. The computer system includes one or more processors 896 configured to control the operation of the computer system 800. The processor(s) 896 can include any type of microprocessor or central processing unit (CPU), including programmable general-purpose or special-purpose microprocessors and/or any one of a variety of proprietary or commercially available single or multi-processor systems. The computer system 800 also includes one or more memories 897 configured to provide temporary storage for code to be executed by the processor(s) 896 or for data acquired from one or more users, storage devices, and/or databases. The memory 897 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system are coupled to a bus system 812. The illustrated bus system 812 is an abstraction that represents any one or more separate physical busses, communication lines/interfaces, and/or multi-drop or point-to-point connections, connected by appropriate bridges, adapters, and/or controllers. The computer system 800 also includes one or more network interface(s) 899 (also referred to herein as a communications interface), one or more input/output (IO) interface(s) 880, and one or more storage device(s) 810.

The communications interface(s) 899 are configured to enable the computer system to communicate with remote devices, e.g., other computer systems and/or devices 500 or housings 630, over a network, and can be, for example, remote desktop connection interfaces, Ethernet adapters, and/or other local area network (LAN) adapters. The IO interface(s) 880 include one or more interface components to connect the computer system 800 with other electronic equipment. For example, the IO interface(s) 880 can include high speed data ports, such as universal serial bus (USB) ports, 1394 ports, Wi-Fi, Bluetooth, etc. Additionally, the computer system 800 can be accessible to a human user, and thus the IO interface(s) 880 can include displays, speakers, keyboards, pointing devices, and/or various other video, audio, or alphanumeric interfaces. The storage device(s) 810 include any conventional medium for storing data in a non-volatile and/or non-transient manner. The storage device(s) 810 are thus configured to hold data and/or instructions in a persistent state in which the value(s) are retained despite interruption of power to the computer system. The storage device(s) 810 can include one or more hard disk drives, flash drives, USB drives, optical drives, various media cards, diskettes, compact discs, and/or any combination thereof and can be directly connected to the computer system or remotely connected thereto, such as over a network. In an exemplary embodiment, the storage device(s) 810 include a tangible or non-transitory computer readable medium configured to store data, e.g., a hard disk drive, a flash drive, a USB drive, an optical drive, a media card, a diskette, or a compact disc.

The elements illustrated in FIG. 8 can be some or all of the elements of a single physical machine. In addition, not all of the illustrated elements need to be located on or in the same physical machine.

The computer system 800 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 800 can also include a web server for generating and/or delivering the web pages to client computer systems.

As shown in FIG. 7, the computer system 800 of FIG. 8 as described above may form the components of the central computer system 700 which is in communication with one or more of the device computer systems 90 of the one or more individual drug administration devices 500 or housings 630 and/or in communication with one or more other elements, such as one or more surgical instruments. Data, such as operational data of the devices 500 or housings 630, medical data acquired of patients by such devices 500 or housings 630, operational data of the surgical instruments, medical data acquired of patients by such surgical instruments, can be exchanged between the central and device computer systems 700, 90.

As mentioned the computer system 800 as described above can also form the components of a device computer system 90 which is integrated into or in close proximity to the drug administration device 500 or housing 630. In this regard, the one or more processors 896 correspond to the processor 96, the network interface 799 corresponds to the communications interface 99, the IO interface 880 corresponds to the user interface 80, and the memory 897 corresponds to the memory 97. Moreover, the additional storage 810 can also be present in device computer system 90.

In an exemplary embodiment, the computer system 800 can form the device computer system 90 as a single unit, e.g., contained within a single drug administration device housing 30, contained within a single package 35 for one or more drug administration devices 500, or a housing 630 that includes a plurality of drug holders 610. The computer system 800 can form the central computer system 700 as a single unit, as a single server, or as a single tower.

The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system can also include any of a variety of other software and/or hardware components, including by way of example, operating systems and database management systems. Although an exemplary computer system is depicted and described herein, it will be appreciated by a person skilled in the art that this is for sake of generality and convenience. In other embodiments, the computer system may differ in architecture and operation from that shown and described here. For example, the memory 897 and the storage device 810 can be integrated together, or the communications interface 899 can be omitted if communication with another computer system is not necessary.

Surgical Hubs

In an exemplary embodiment, the computer system to which data regarding drug administration devices and/or surgical instruments is communicated includes a surgical hub. Exemplary examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0201114 entitled "Adaptive Control Program Updates For Surgical Hubs" filed Mar. 29, 2018, U.S. Pat. Pub. No. 2019/0207857 entitled "Surgical Network Determination Of Prioritization Of Communication, Interaction, Or Processing Based On System Or Device Needs" filed Nov. 6, 2018, and U.S. Pat. Pub. No. 2019/0206555 entitled "Cloud-based Medical Analytics For Customization And Recommendations To A User" filed Mar. 29, 2018, which are hereby incorporated by reference in their entireties.

In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as one or more surgical instruments that are used to conduct medical procedures on patients and/or one or more drug administration device that are used to administer one or more drugs to patients during performance of medical procedures. The surgical hubs provide a wide array of functionality to improve the outcomes of medical procedures. The data generated by the various surgical devices, drug administration devices, and surgical hubs about the patient and the medical procedure may be transmitted to the cloud-based medical analytics system. This data may then be aggregated with similar data gathered from many other surgical hubs, drug administration devices, and surgical instruments located at other medical facilities. Various patterns and correlations may be found through the cloud-based analytics system analyzing the collected data. Improvements in the techniques used to generate the data may be generated as a result, and these improvements may then be disseminated to the various surgical hubs, drug administration devices, and surgical instruments. Due to the interconnectedness of all of the aforementioned components, improvements in medical procedures and practices may be found that otherwise may not be found if the many components were not so interconnected. Various examples of structures and functions of these various components are described in more detail in previously mentioned U.S. Pat. Pub. No. 2019/0200844 entitled "Method Of Hub Communication, Processing, Storage And Display" filed Dec. 4, 2018, U.S. Pat. Pub. No. 2019/0201114 entitled "Adaptive Control Program Updates For Surgical Hubs" filed Mar. 29, 2018, U.S. Pat. Pub. No. 2019/0207857 entitled "Surgical Network Determination Of Prioritization Of Communication, Interaction, Or Processing Based On System Or Device Needs" filed Nov. 6, 2018, and U.S. Pat. Pub. No. 2019/0206555 entitled "Cloud-based Medical Analytics For Customization And Recommendations To A User" filed Mar. 29, 2018.

Figure 9:
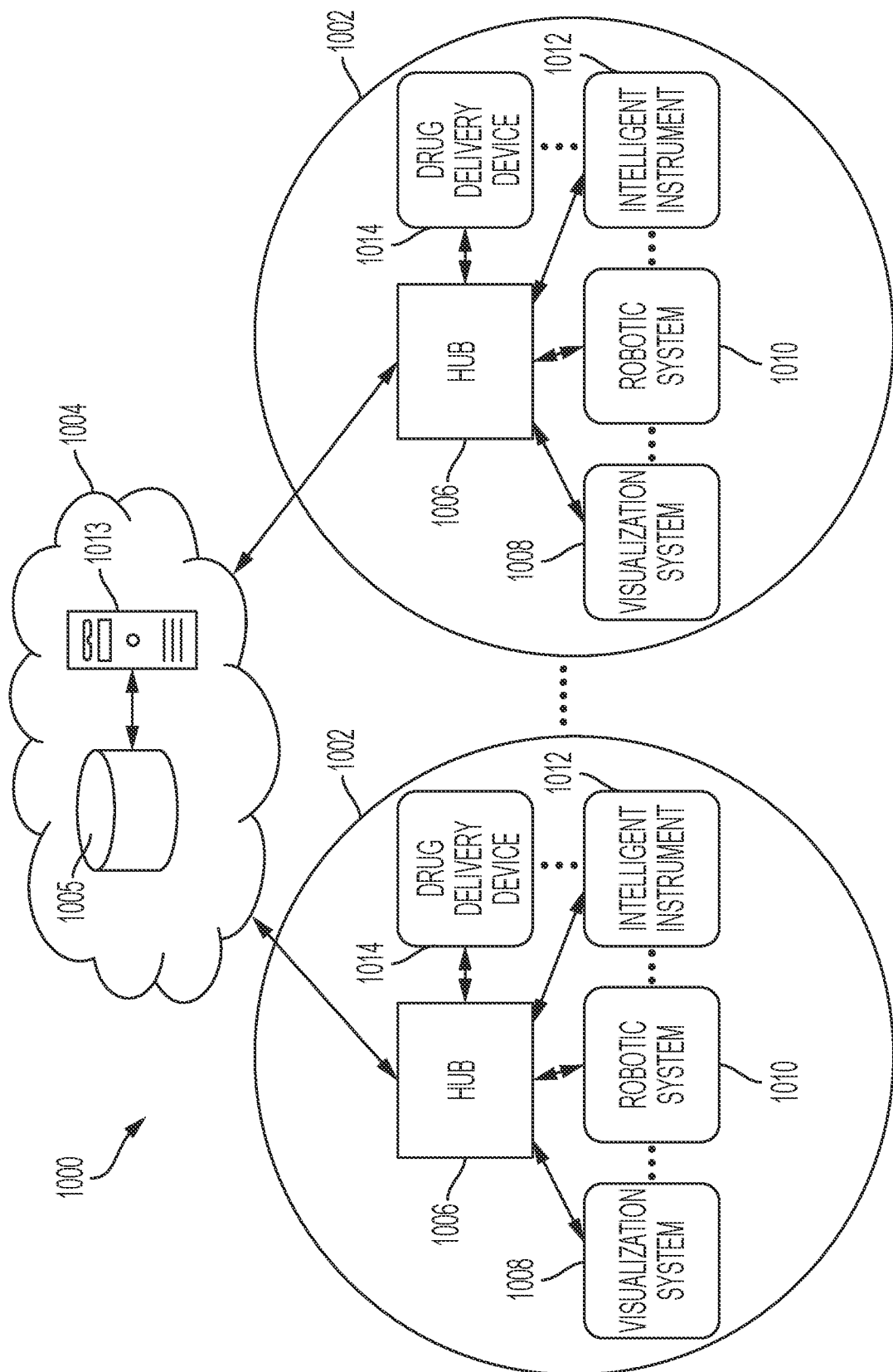
FIG. 9 is a schematic view of one embodiment of a computer-implemented interactive surgical system.

FIG. 9 illustrates an embodiment of a computer-implemented interactive surgical system 1000 that includes one or more surgical systems 1002 and a cloud-based system (e.g., a cloud 1004 that can include a remote server 1013 coupled to a storage device 1005). Each surgical system 1002 includes at least one surgical hub 1006 in communication with the cloud 1004. In one example, as illustrated in FIG. 9, the surgical system 1002 includes a visualization system 1008, a robotic system 1010, a handheld intelligent surgical instrument 1012, and a drug delivery device 1014, which are configured to communicate with one another and/or the hub 1006. The surgical system 1002 can include an M number of hubs 1006, an N number of visualization systems 1008, an O number of robotic systems 1010, a P number of handheld intelligent surgical instruments 1012, and a Q number of drug delivery devices 1014, where M, N, O, P, and Q are integers greater than or equal to one that may or may not be equal to any one or more of each other. Various exemplary drug delivery devices are described above. Various exemplary examples of suitable robotic systems, visualization systems, cloud-based analytics, and surgical instruments that can be used in a computer-implemented interactive surgical system are further described in previously mentioned U.S. Pat. Pub. No. 2019/0200844 entitled "Method Of Hub Communication, Processing, Storage And Display" filed Dec. 4, 2018, U.S. Pat. Pub. No. 2019/0201114 entitled "Adaptive Control Program Updates For Surgical Hubs" filed Mar. 29, 2018, U.S. Pat. Pub. No. 2019/0207857 entitled "Surgical Network Determination Of Prioritization Of Communication, Interaction, Or Processing Based On System Or Device Needs" filed Nov. 6, 2018, and U.S. Pat. Pub. No. 2019/0206555 entitled "Cloud-based Medical Analytics For Customization And Recommendations To A User" filed Mar. 29, 2018.

Figure 10:
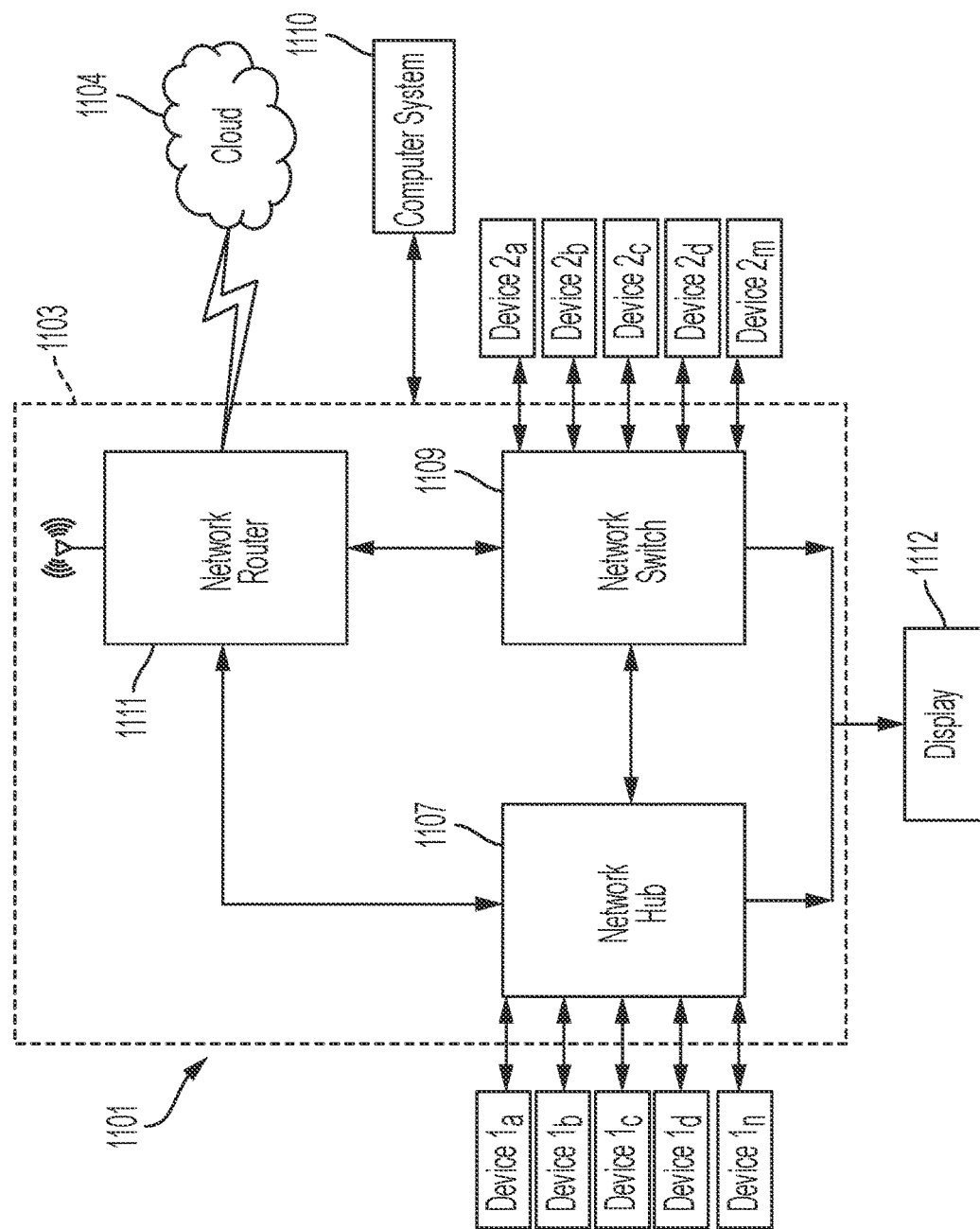
FIG. 10 is a schematic view of one embodiment of a surgical data network.

FIG. 10 illustrates one example of a surgical data network 1101 including a modular communication hub 1103, e.g., the hub 1006, configured to connect modular devices located in one or more operating theaters of a healthcare facility, or any room in a healthcare facility specially equipped for surgical operations, to a cloud-based system including the cloud 1104 that includes a remote server 1113 coupled to a storage device 1105, e.g., the cloud 1004 that includes the remote server 113 coupled to the storage device 1005. The modular communication hub 1103 includes a network hub 1107 and/or a network switch 1109 in communication with a network router 1111. The network hub 1107, the network switch 1109, and the network router 1111 define the communication hub's communications interface. The modular communication hub 1103 also can be coupled to a local computer system 1110 to provide local computer processing and data manipulation. The surgical data network 1101 can be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 1107 or network switch 1109. An "intelligent surgical data network" may be referred to as a "manageable hub" or "manageable switch." A switching hub reads the destination address of each packet and then forwards the packet to the correct port.

Modular devices $1_a$-$1_n$, e.g., any number of surgical instruments such as instruments 1012 and/or any number of drug delivery devices such as devices 1014, located in the operating theater can be coupled to the modular communication hub 1103. The network hub 1107 and/or the network switch 1109 can be coupled to a network router 1111 to connect the devices $1_a$-$1_n$ to the cloud 1104 or the local computer system 1110. Data associated with the devices $1_a$-$1_n$ can be transferred to cloud-based computers via the router for remote data processing and manipulation. Data associated with the devices $1_a$-$1_n$ can also be transferred to the local computer system 1110 for local data processing and manipulation. Modular devices $2_a$-$2_m$ located in the same operating theater also can be coupled to a network switch 1109. The network switch 1109 can be coupled to the network hub 1107 and/or the network router 1111 to connect to the devices $2_a$-$2_m$ to the cloud 1104. Data associated with the devices $2_a$-$2_n$ can be transferred to the cloud 1104 via the network router 1111 for data processing and manipulation. Data associated with the devices $2_a$-$2_m$ can also be transferred to the local computer system 1110 for local data processing and manipulation. The numbers n, m of the devices $1_a$-$1_n$/$2_a$-$2_m$ can be the same as or different from one another.

A person skilled in the art will appreciate that the surgical data network 1101 can be expanded by interconnecting multiple network hubs 1107 and/or multiple network switches 1109 with multiple network routers 1111. The modular communication hub 1103 can be contained in a modular control tower configured to receive multiple devices $1_a$-$1_n$/$2_a$-$2_m$. The local computer system 1110 also can be contained in a modular control tower. The modular communication hub 1103 is connected to a display 1112 to display images obtained by at least some of the devices $1_a$-$1_n$/$2_a$-$2_m$, for example during surgical procedures.

The surgical data network 1101 can include a combination of network hub(s), network switch(es), and network router(s) connecting the devices $1_a$-$1_n$/$2_a$-$2_m$ to the cloud 1104. Any one of or all of the devices $1_a$-$1_n$/$2_a$-$2_m$ coupled to the network hub 1107 or network switch 1109 can collect data in real time and transfer the data to cloud computers for data processing and manipulation. Alternatively or in addition, any one or all of the devices $1_a$-$1_n$/$2_a$-$2_m$ coupled to the network hub 1107 or network switch 1109 can transfer previously collected data, such as sensor data, to cloud computers for data processing and manipulation, e.g., once the one or all of the devices $1_a$-$1_n$/$2_a$-$2_m$ is operatively connected to the cloud 1104 via the communication hub 1103. A person skilled in the art will appreciate that cloud computing relies on sharing computing resources rather than having local servers or personal devices to handle software applications. The term "cloud" can be used as a metaphor for "the Internet," although the term is not limited as such. Accordingly, the term "cloud computing" may be used herein to refer to "a type of Internet-based computing," where different services, such as servers, storage, and applications, are delivered to the modular communication hub 1103 and/or the computer system 1110 located in the surgical theater (e.g., a fixed, mobile, temporary, or field operating room or space) and to devices connected to the modular communication hub 1103 and/or the computer system 1110 through the Internet. The cloud infrastructure can be maintained by a cloud service provider. In this context, the cloud service provider can be the entity that coordinates the usage and control of the devices $1_a$-$1_n$/$2_a$-$2_m$ located in one or more operating theaters. The cloud computing services can perform a large number of calculations based on the data gathered by smart surgical instruments, smart drug delivery devices, robots, and other computerized devices located in the operating theater. The hub hardware enables multiple devices or connections to be connected to a computer that communicates with the cloud computing resources and storage.

Applying cloud computer data processing techniques on the data collected by the devices $1_a$-$1_n$/$2_a$-$2_m$, the surgical data network may provide improved surgical outcomes, reduced costs, and/or improved patient satisfaction. At least some of the devices $1_a$-$1_n$/$2_a$-$2_m$, e.g., one or more of the surgical instruments 1012, can be employed to view tissue states to assess leaks or perfusion of sealed tissue after a tissue sealing and cutting procedure. At least some of the devices $1_a$-$1_n$/$2_a$-$2_m$, e.g., one or more of the surgical instruments 1012, can be employed to identify pathology, such as the effects of diseases, using the cloud-based computing to examine data including images of samples of body tissue for diagnostic purposes. This includes localization and margin confirmation of tissue and phenotypes. At least some of the devices $1_a$-$1_n$/$2_a$-$2_m$, e.g., one or more of the surgical instruments 1012, can be employed to identify anatomical structures of the body using a variety of sensors integrated with imaging devices and techniques such as overlaying images captured by multiple imaging devices. At least some of the devices $1_a$-$1_n$/$2_a$-$2_m$, e.g., one or more of the drug delivery devices 1014, can be employed to identify dimensions of a patient's bariatric sleeve in bariatric surgical intervention using, e.g., an insulin pump, to facilitate visualization of the sleeve. The data gathered by the devices $1_a$-$1_n$/$2_a$-$2_m$, including image data, can be transferred to the cloud 1104 or the local computer system 1110 or both for data processing and manipulation including image processing and manipulation.

The data can be analyzed to improve surgical procedure outcomes by determining if further treatment, such as the application of endoscopic intervention, emerging technologies, a targeted radiation, targeted intervention, precise robotics to tissue-specific sites and conditions, and drug administration may be pursued. Such data analysis can further employ outcome analytics processing, and using standardized approaches may provide beneficial feedback to either confirm surgical treatments and the behavior of the surgeon or suggest modifications to surgical treatments, surgeon behavior, drug delivery devices, and/or drugs.

The operating theater devices $1_a$-$1_n$ can be connected to the modular communication hub 1103 over a wired channel or a wireless channel depending on the configuration of the devices $1_a$-$1_n$ to a network hub. The network hub 1107 can be implemented as a local network broadcast device that works on the physical layer of the Open System Interconnection (OSI) model. The network hub provides connectivity to the devices $1_a$-$1_n$ located in the same operating theater network. The network hub 1107 collects data in the form of packets and sends them to the router 1111 in half duplex mode. The network hub 1107 does not store any media access control/Internet Protocol (MAC/IP) to transfer the device data. Only one of the devices $1_a$-$1_n$ can send data at a time through the network hub 1107. The network hub 1107 has no routing tables or intelligence regarding where to send information and broadcasts all network data across each connection and to a remote server over the cloud 1104. The network hub 1107 can detect basic network errors such as collisions, but having all information broadcast to multiple ports can be a security risk and cause bottlenecks.

The operating theater devices $2_a$-$2_m$ can be connected to a network switch 1109 over a wired channel or a wireless channel. The network switch 1109 works in the data link layer of the OSI model. The network switch 1109 is a multicast device for connecting the devices $2_a$-$2_m$ located in the same operating theater to the network. The network switch 1109 sends data in the form of frames to the network router 1111 and works in full duplex mode. Multiple devices $2_a$-$2_m$ can send data at the same time through the network switch 1109. The network switch 1109 stores and uses MAC addresses of the devices $2_a$-$2_m$ to transfer data.

The network hub 1107 and/or the network switch 1109 are coupled to the network router 1111 for connection to the cloud 1104. The network router 1111 works in the network layer of the OSI model. The network router 1111 creates a route for transmitting data packets received from the network hub 1107 and/or the network switch 1111 to cloud-based computer resources for further processing and manipulation of the data collected by any one of or all the devices $1_a$-$1_n$/$2_a$-$2_m$. The network router 1111 can be employed to connect two or more different networks located in different locations, such as, for example, different operating theaters of the same healthcare facility or different networks located in different operating theaters of different healthcare facilities. The network router 1111 sends data in the form of packets to the cloud 1104 and works in full duplex mode. Multiple devices can send data at the same time. The network router 1111 uses IP addresses to transfer data.

In one example, the network hub 1107 can be implemented as a USB hub, which allows multiple USB devices to be connected to a host computer. The USB hub can expand a single USB port into several tiers so that there are more ports available to connect devices to the host system computer. The network hub 1107 can include wired or wireless capabilities to receive information over a wired channel or a wireless channel. A wireless USB short-range, high-bandwidth wireless radio communication protocol cab be employed for communication between the devices $1_a$-$1_n$ and devices $2_a$-$2_m$ located in the operating theater.

In other examples, the operating theater devices $1_a$-$1_n$/$2_a$-$2_m$ can communicate to the modular communication hub 1103 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices $1_a$-$1_n$/$2_a$-$2_m$ can communicate to the modular communication hub 1103 via a number of wireless or wired communication standards or protocols, including but not limited to Wi-Fi (IEEE 802.11 family), WiMAX (IEEE 802.16 family), IEEE 802.20, long-term evolution (LIE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module can include a plurality of communication modules. For example, a first communication module may be dedicated to shorter-range wireless communications such as Wi-Fi and Bluetooth, and a second communication module can be dedicated to longer-range wireless communications such as GPS, EDGE, GPRS, CDMA, WiMAX, LTE, Ev-DO, and others.

The modular communication hub 1103 can serve as a central connection for one or all of the operating theater devices $1_a$-$1_n$/$2_a$-$2_m$ and handle a data type known as frames. Frames carry the data generated by the devices $1_a$-$1_n$/$2_a$-$2_m$. When a frame is received by the modular communication hub 1103, it is amplified and transmitted to the network router 1111, which transfers the data to the cloud computing resources by using a number of wireless or wired communication standards or protocols, as described herein.

The modular communication hub 1103 can be used as a standalone device or be connected to compatible network hubs and network switches to form a larger network. The modular communication hub 1103 is generally easy to install, configure, and maintain, making it a good option for networking the operating theater devices $1_a$-$1_n$/$2_a$-$2_m$.

Data Monitoring And Communication

A drug administration device, e.g., any of the autoinjector 100 of FIG. 1, the infusion pump 200 of FIG. 2, the inhaler 300 of FIG. 3, the drug administration device 500 of FIG. 5, and other drug administration devices described herein, can be configured to electronically communicate data over a network to another device, e.g., the central computer system 700 of FIG. 7, the surgical hub 1006 of FIG. 9, the remote server 1013 of the cloud 1004 of FIG. 9, and other computer systems described herein. The following discussion discusses a drug administration device but similarly applies to a housing, e.g., the housing 630 of FIG. 6. The data can include any of a number of types of information related to the drug administration device, the drug dispensable drug administration device, and/or a patient to whom the drug administration device is configured to deliver the drug in a surgical setting and/or otherwise. In an exemplary embodiment, the data includes data sensed by one or more sensors of the drug administration device. The computer system that receives the data from the drug administration device (and/or other computer system that receives the data therefrom) can be configured to use the data to help improve the patient's experience with the drug administration device, the patient's experience with the drug, other patients' experiences with a same type of drug administration device as the drug administration device, other patients' experiences with the same drug, other patients' experiences with a different drug, and/or a health care provider's (HCP) understanding of the drug administration device and/or the drug. The computer system that receives the data from the drug administration device (and/or other computer system that receives the data therefrom) can be configured to analyze the data received from the drug administration device in a variety of ways to help achieve one or more of these and/or other goals, such as by any one or more of correlating the patient's use of the drug with the patient's clinical outcome, performing a cost analysis that includes comparing the patient's clinical outcome with clinical outcomes of other patients receiving a different drug than the drug delivered to the patient via the drug administration device, comparing side effects experienced by the patient with side effects experienced by other patients receiving a different drug than the drug delivered to the patient, determining whether the drug was delivered to the patient in compliance with the patient's treatment plan, identifying a malfunction in the administration of the drug, determining that additional data is needed from the drug administration device and triggering a request for the additional data to be wirelessly transmitted from the other device to the drug administration device, and predictive modeling of the patient's clinical outcome. For example, in at least some embodiments, a surgical hub can receive data from a drug administration device and can analyze the data and/or communicate the data to a cloud configured to analyze the data. The computer system that receives the data from the drug administration device (and/or other computer system that receives the data therefrom) can also be configured to receive data sensed by one or more sensors of each of one or more additional drug administration devices to increase the data set available for analysis and thus improve the overall analysis by having a larger data set.

The drug administration device providing data to the other device, e.g., the central computer system 700 of FIG. 7, the surgical hub 1006 of FIG. 9, the remote server 1013 of the cloud 1004 of FIG. 9, etc., may provide any of a number of benefits that cannot be achieved easily or at all if the data is unavailable or is collected in another way. For example, a user such as a patient, a patient's care provider, or a medical professional manually reporting information about use of the drug administration device and/or the drug results in delayed communication of information from a time of drug delivery and may not include all relevant information in sufficient detail due to the user's misremembering of details and/or the user's inability to accurately observe the information. For another example, data can be communicated from the drug administration device to the central computer system 700 of FIG. 7, the surgical hub 1006 of FIG. 9, the remote server 1013 of the cloud 1004 of FIG. 9, etc., according to a predetermined automatic schedule, which may help ensure that all relevant data is received by the other device in a predictable and timely manner. For yet another example, some types of information can be difficult or impossible for a user of the drug administration device to detect, such as a precise amount of the drug delivered to the patient in a single dose, a temperature of the drug, GPS location of the patient when a dose of the drug is delivered to the patient, etc. A sensor of the drug administration device can, however, as discussed herein, be configured to sense information that is difficult or impossible for a user of the drug administration device to detect, and thus allow this data to be considered in analysis performed by the other device. For still another example, the drug administration device can be one of multiple drug delivery devices all providing the same one or more types of sensed data to the other device, e.g., the central computer system 700 of FIG. 7, the surgical hub 1006 of FIG. 9, the remote server 1013 of the cloud 1004 of FIG. 9, etc., thereby allowing the other device to predictably receive multiple data sets that can be compared with one another to provide medical professionals and/or manufacturers with data useful in, e.g., developing patient treatment plans, modifying existing patient treatment plans, selecting a drug for a patient, selecting a drug administration device for a patient, designing drug administration devices, and/or upgrading existing drug administration devices.

The sensors described herein can be configured to gather data regarding a variety of conditions, such as device conditions (e.g., as sensed by the device sensor 92), environmental conditions (e.g., as sensed by the environment sensor 94), and location conditions (e.g., as sensed by the location sensor 98). Examples of conditions include geographic location (e.g., as sensed by a location sensor configured to sense GPS or other location), time (e.g., as sensed by a timer or a clock device such as an atomic clock), date (e.g., as sensed by a timer), temperature (e.g., as sensed by a temperature sensor such as a thermistor, a thermocoupler, a thermistor, etc.), ultraviolet (UV) exposure (e.g., as sensed by a UV sensor configured to sense UV level), humidity (e.g., as sensed by a humidity sensor configured to sense humidity level such as a thermistor, a humistor, a hygrometer, etc.), pressure (e.g., as sensed by a pressure sensor), angular rate (e.g., as sensed by an inertial measurement unit (IMU) or MARG (magnetic, angular rate, and gravity) sensor), body orientation (e.g., using an IMU, an accelerometer, etc.), current of a motor used in delivering the drug (e.g., using a current sensor), blood oxygenation level (e.g., using a blood oxygen sensor), sun exposure (e.g., using a UV sensor, etc.), osmolality (e.g., using a blood monitor, etc.), and air quality (e.g., using a UV sensor, etc.). The conditions can be physiological conditions and/or situational conditions of the patient. Various different physiological conditions can be monitored, such as blood sugar level (e.g., using a glucose monitor, etc.), blood pressure (e.g., using a blood pressure monitor, etc.), perspiration level (e.g., using a fluid sensor, etc.), heart rate (e.g., using a heart rate monitor, etc.), etc. A number of different situational conditions can be monitored, such as core temperature, (e.g., using a temperature sensor such as a thermistor, a thermocoupler, a thermistor, etc.), tremor detection (using an accelerometer, etc.), time of day (e.g., using a timer, etc.), date (e.g., using a timer, etc.), patient activity level (e.g., using a motion sensor, etc.), blood pressure (e.g., using a blood pressure monitor, etc.), metabolic rate (e.g., using heart rate as discussed herein, etc.), altitude (e.g., using an altimeter, etc.), temperature of the drug (e.g., using a temperature sensor such as a thermistor, a thermocoupler, a thermistor, etc.), viscosity of the drug (e.g., using a viscometer, etc.), GPS information (e.g., using a location sensor, etc.), weather information (e.g., using a temperature sensor, humidity sensor, etc.), room or external temperature (e.g., using a temperature sensor such as a thermistor, a thermocoupler, a thermistor, etc.), angular rate (e.g., using an inertial measurement unit (IMU) or MARG (magnetic, angular rate, and gravity) sensor), body orientation (e.g., using an IMU, an accelerometer, etc.), current of a motor used in delivering the drug (e.g., using a current sensor), blood oxygenation level (e.g., using a blood oxygen sensor), sun exposure (e.g., using a UV sensor, etc.), osmolality (e.g., using a blood monitor, etc.), and air quality (e.g., using a UV sensor, etc.), inflammatory response, one or more images and/or videos of the patient and/or an environment in which the patient is located (for example, to analyze food intake; to determine whether solid food or liquid is being consumed; to determine a location or activity of the patient; to determine a condition of the patient such as skin reaction, breathing, eye dilation, voice characteristics such as tone and pitch; etc.), user-input data such as general well-being, pain score, or a cycle time between flare ups of a particular ailment, etc.

In various embodiments, a sensor includes an image capturing device such as a camera, and a processor is configured to analyze image(s) and/or video(s) captured by the image capturing device, such as to analyze any food/drink intake and/or patient skin reaction to the drug. U.S. Pat. Pub. No. 2012/0330684 entitled "Medication Verification And Dispensing" published Dec. 27, 2012, which is incorporated by reference herein in its entirety, further describes image capturing devices. Analyzing food/drink intake can include analysis of images captured by the image capturing device to visually identify a variety of types of information about food and/or drink that a user is consuming, such as food and/or drink type, food and/or drink amount, amount of food remaining on plate, amount of drink remaining in a cup, etc. U.S. Pat. Pub. No. 2011/0295337 entitled "Systems and Methods For Regulating Metabolic Hormone Producing Tissue" filed on Dec. 1, 2011, U.S. Pat. No. 8,696,616 entitled "Obesity Therapy And Heart Rate Variability" issued Apr. 15, 2014, U.S. Pat. No. 9,427,580 entitled "Devices And Methods For The Treatment Of Metabolic Disorders" issued Aug. 30, 2016, and U.S. Pat. No. 9,168,000 entitled "Meal Detection Devices And Methods" issued Oct. 27, 2015, which are hereby incorporated by reference in their entireties, further describe identifying types of information about food and/or drink. Detecting occurrences of eating/drinking with certainty is important for safety, efficacy, and cost, and can be combined with sensed information through situational awareness, as discussed above, to increase the accuracy of meal (food and/or drink) detection.

U.S. Pat. Pub. No. 2002/0014951 entitled "Remote Control For A Hospital Bed" published Feb. 7, 2002, and U.S. Pat. Pub. No. 2007/0251835 entitled "Subnetwork Synchronization And Variable Transmit Synchronization Techniques For A Wireless Medical Device Network" published Nov. 1, 2007, further discuss various sensors and are hereby incorporated by reference herein in their entireties.

In at least some embodiments, the drug administration device's processor and/or another processor (e.g., a processor of a surgical hub, a processor of a cloud-based server, or other processor) is configured to use a hierarchy in terms of how data from each of a plurality of sensors is used compared to each other, where each of the sensors is configured to monitor a different condition. The hierarchy prioritizes one of the sensors over the other(s) such that one sensor acts as a primary sensor and the other sensor(s) act as secondary or ancillary sensor(s). In such embodiments, the condition measured by the primary sensor can be considered to be the primary or defining condition, and condition(s) measured by the secondary sensor(s) can be secondary or influencing conditions on the primary condition. This prioritization or hierarchy of conditions (and thus data) can be helpful, for example, when the drug administration device is used for a treatment that includes one controlling condition and one or more secondary conditions that may influence or assist in monitoring the controlling condition, for example when measuring blood pressure when administering blood pressure medication or when measuring blood sugar level when administering insulin. While secondary conditions can help in monitoring high blood pressure or low blood sugar, the conditions of primary concern in each example is blood pressure itself or blood sugar level itself. The prioritization of data and inputs from one or more secondary sensors based on the hierarchical relationship can be customizable based on desired patient outcomes, various expected or anticipated side-effects, the drug being administered, time of day, location, activity level, caloric intake, physical activity, etc. The drug administration device can thus have associated therewith a predefined hierarchy of levels or severity of effect on dosage based on the sensed conditions from the sensor(s). A medical professional or unlearned algorithm within the drug administration device itself and/or a computer system (e.g., a surgical hub, a cloud-based system, etc.) in communication with the drug administration device can optionally adjust the priority of the levels or reorder the importance of the various sensed data and inputs as a result of dosing amounts and/or dosing timelines. Because so much data can be generated by using a plurality of sensors and because data from one sensor may contradict data from another sensor in some instances, effectively using situational awareness to personalize drug administration to each patient may benefit from prioritization and relative weighing of multiple sources of information to arrive at a most correct conclusion or recommendation to best help the patient. This hierarchy of prioritization can be customized for a specific patient based on how the patient presents in any one moment or over time, therefore providing an adaptive device with re-orderable hierarchal relationships.

As mentioned above, the hierarchical arrangement can be used in a variety of ways, for example to verify a physiological result such that data from one or more sensors is considered to adjust at least one variable parameter of the drug administration device's control program, discussed further below, to proactively manage any anticipated negative effect on the primary characteristic being measured. The hierarchy between various sensors can be predefined; can be adaptable based on user input, such as providing input through a drug administration device's and/or a computer system's user interface; can be adaptable based on a processor, an algorithm, any analyzed data, etc.; and/or can be adaptable through contact with remote computer systems, doctors, remote-care providers, etc.

In general, a primary condition for a drug administration device can be a control measure, and secondary condition(s) or measures can be data taken from sources surrounding the primary condition and/or sources that can influence and/or be influenced by the primary source. For example, blood sugar level is a primary condition for insulin delivery, but blood pressure is a primary condition for various blood pressure medications. Additionally, sources surrounding the primary source can take a variety of different forms, such as glucose level (for example, as measured by a micro needle application and/or sweat analysis); blood pressure (for example, as measured by various wearable cuffs); hydration (for example, as measured by perspiration level); heart rate and/or activity level (for example, as measured by various metabolic consumption rates, sitting or sedentary motion determined by elevation changes, various gyroscopes); EKG cycle; heart rate variability; various acute effects or activities to trigger measurement (such as sleep or sleep quality detection and/or meal detection, for example by analyzing one or more images of the patient, receiving input from the patient, etc.); discernment between eating and drinking; various long term effects to monitor any changes that might inform a new diagnoses or provide alerts to seek evaluation for any possible new conditions; core temperature; tremor detection; patient held/worn camera image analysis; time of day; digital calendar information; GPS outputs; device activity; any user interaction with the drug administration device; etc.

Additionally, numerous means for being aware of any surrounding situation during administration of the drug from the drug administration device are possible, providing a variety of types of situational awareness that one or more drug administration devices can use. As further examples, forms of cognitive analysis can be performed on the patient by combining small interactions with the patient and various automated sensors on or around the patient to determine cognitive effects of any drug dosage on the patient. Various measured reactions to drug dosages can also be analyzed, such as timing to a first effect, effect duration, magnitude of effect, etc. Ending continued application of a drug can be one result, however there are many other examples where such an action can be taken. For example, if a biologic or drug is being delivered on an ongoing basis, the plurality of sensors can allow detection of an onset of a complex biologic response to the biologic or drug, and a drug administration device can have the ability to affect, retard, or end the continued application of the biologic or drug. Thus, drug administration devices, surgical hubs, and/or other computer systems described herein can be configured to provide detection of and an automated response to collateral physiologic reactions to any continuous biologic introduction. For example, injection reactions can be an issue for some biologics, especially when delivered through an IV given delivery times and the continuous administration. Thus, drug administration devices, surgical hubs, and/or other computer systems described herein can be configured to detect various onsets of injection reactions, such as through sensor(s), and consequently stop or slow down delivery of the drug. In at least some embodiments, drug administration devices described herein can be configured to deliver other medication(s) to stop, lessen, or counteract the drug injection reaction. As another example, cytokine release syndrome is a form of systemic inflammatory response syndrome that can arise from an adverse effect of some monoclonal antibody drugs, as well as adoptive T-cell therapies. Once a drug administration device, or other system in communication with the drug administration device, detects pro- and anti-inflammatory components above a predetermined threshold in a patient, the drug administration device can be configured to reduce or stop the introduction of the treatment. In such an example, the drug administration device, surgical hubs, and/or other computer systems can also be configured to notify medical personnel or introduce a canceling agent to accelerate the reduction of the response. If the injection response is great enough as defined by predefined criteria, the drug administration device can be configured to automatically escalate its response, or a surgical hub (and/or other computer system) can be configured to cause the drug administration device to escalate its response, from a passive indication or reduction of dosage to a more active warning notification or introductions of other active countermeasures. Even when medical intervention is required, such as requiring a patient to go into a hospital for emergency treatment or altering a pre-operative plan during surgery, the drug administration devices and surgical hubs (and other computer systems) described herein can be configured to use biometric data to detect changes in the patient's body, such as body temperature or heart rate, that typically proceed a serious effect. The drug administration device and/or the surgical hub (and/or other computer system) can be configured to notify the patient and/or medical personnel of the imminent effect to allow the patient and/or medical personnel to take preemptive action, such as taking medication at home before then going into the hospital before one or more major side effects take place, preparing another drug for delivery, etc. This early warning can improve patient outcomes by reducing any negative consequences.

Using the drug administration device 500 of FIG. 5 and the computer system 700 of FIG. 7 by way of example for clarity and ease of description of implementations provided herein, the drug administration device 500 can be configured to transmit data indicative of the information sensed by the drug administration device's one or more sensors 92, 94, 98 to the computer system 700 automatically according to a predetermined schedule, e.g., transmit data every hour, every three hours, every twelve hours, once daily, every time the drug administration device 500 delivers a dose, every other time the drug administration device 500 delivers a dose, etc. In this way, the system 700 can regularly receive data for analysis and neither a user of the drug administration device 500 nor the system 700 need prompt for the data transmission. The predetermined schedule can be programmed into the drug administration device's memory 97, in which case the drug administration device 500 transmits data without prompting from the system 700, or the predetermined schedule can be programmed into the system 700, in which case the system 700 transmits a request for data to the drug administration device 500 which transmits data in reply to the system 700. In an exemplary embodiment the predetermined schedule is the same for all sensed data, which may help conserve device power and resources, but the predetermined schedule can be different for data monitored by different sensors 92, 94, 98 of the drug administration device 500, which may help the system 700 have more time available for analysis.

In addition or in alternative to the drug administration device 500 being configured to transmit data indicative of the information sensed by the drug administration device's one or more sensors 92, 94, 98 automatically, the drug administration device 500 can be configured to transmit data to the system 700 on demand in reply to a request for data from the system 700 to the drug administration device 500. Transmitting data on demand may help conserve device power and resources and/or may help ensure that the system 700 only receives data it needs to perform a particular analysis. The system 700 can be configured to transmit the request to the drug administration device 500 according to a predetermined schedule, e.g., transmit data every hour, every three hours, every twelve hours, once daily, etc., and/or can be configured to transmit the request in response to a user input to the system 700 requesting that the drug administration device 500 be queried for sensed information.

In addition or in alternative to the drug administration device 500 being configured to transmit data indicative of the information sensed by the device's one or more sensors 92, 94, 98 according to a predetermined schedule and/or on demand from the system 700, the drug administration device 500 can be configured to be manually triggered by a user to transmit data on demand to the computer system 700, such as by user input to the user interface 80. Such on demand data transmission may allow, for example, data related to an event that occurs during performance of a surgical procedure in which the drug administration device 500 is being used to be transmitted to the system 700 for timely analysis related to the event.

The system 700 can be configured to store data received from the drug administration device 500 for analysis at a subsequent time. For example, the system 700 can be configured to perform an analysis on demand in response to a user input to the system 700 requesting one or more types of analysis, such as any one or more of the analyses discussed further below. Performing analysis on demand may help conserve system power and resources and/or may help ensure that the user receives analysis output from the system 700 based on the most current data available to the system 700. For another example, the system 700 can be configured to perform an analysis automatically according to a predetermined schedule, e.g., analyze data every hour, every three hours, every twelve hours, once daily, once the system 700 has received a predetermined number of data transmissions from the drug administration device 500 and/or other drug administration devices so as to have a sufficient amount of new data to include in an analysis, etc. In addition or in alternative, the system 700 can be configured to perform an analysis in response to receipt of the data from the drug administration device 500, e.g., perform an analysis every time the system 700 receives a certain type and/or certain amount of data from the drug administration device 500, etc. Data receipt being a trigger for analysis may help more quickly identify problems with the drug administration device 500 and/or the drug, which in turn may allow the problems to be addressed more quickly by a medical professional and/or a user of the drug administration device 500.

In general, analysis performed by the system 700 uses sensed information from the drug administration device 500 and, in at least some analyses, one or more additional drug administration devices 500. In an exemplary embodiment in which the system 700 is analyzing data received from multiple drug administration devices 500, each of the drug administration devices 500 is of a same type (e.g., is each the same type of autoinjector, inhaler, infusion pump, etc.), is delivering a same type of drug, and/or is delivering the same drug. The data analyzed may therefore yield significant, meaningful results related to a specific type of drug administration device, a specific type of drug, and/or a specific drug. The data collected by the system 700 from the multiple drug administration devices 500 can each be indicative of a same type of sensed information, e.g., drug temperature information, GPS information, dose timing information, etc. Collection of the same types of information from multiple drug administration devices 500 may allow the system 700 to continually review the data and discover trends in the data between patients and relate these trends to patient type, drug administration device type, and functional outcomes. These relationships can be evaluated by the system 700 through multiple algorithms to provide more accurate trends and/or more accurate recommendations, e.g., recommendations of treatments for the patient and their symptoms to result in an optimized outcome, recommendations that result in cost saving, recommendations that result in fewer and/or less severe side effects, etc.

In general, data transmitted from the drug administration device 500 via the network 702 can be received by the system 700. The transmitted data can be aggregated and processed by the system 700. Data including patient medical record data, physician summary data, drug specification data, and financial data associated with the costs of providing care to the patient can be shared via the network 702 and aggregated by the system 700 for use in determining and predicting clinical outcomes, such as that discussed above regarding the surgical hub 1006 communicating with the cloud 1004 of FIG. 9.

In one implementation, the system 700 can be configured to receive data transmitted from the drug administration device 500 and to process the data to correlate a patient's use of a drug with a clinical outcome. A clinical outcome generally includes a measurable change in a state of health, functioning, or quality of life that can occur as a result of a clinical treatment, such as administering a drug in or out of a surgical setting, or receiving a therapeutic treatment. Clinical outcomes can be determined based on data that is received from a patient in response to a prompt, such as a questionnaire or other a similarly formatted self-reported assessment. Clinical outcomes can also be determined based on data that is collected from the patient and is provided by healthcare practitioners. The clinical outcome data can be stored in a database of patient medical files, a hospital information system, or the like and can be transmitted to and/or stored in a memory of the system 700 and/or a memory of another computer system to which the system 700 transmits the data. Although the foregoing describes collecting clinical outcome data via patient self-reporting or by a healthcare provider as inputs to a form or questionnaire, such as a health assessment form which may be implemented on an app that is configured on a mobile computing device, a person skilled in the art will appreciate that clinical outcome data can be captured in other ways and that devices other than mobile computing devices can be used to collect clinical outcome data with or without running an app. A person skilled in the art will appreciate that data can be captured in a variety of ways, e.g., using a camera (stand-alone or integrated into another device such as a mobile phone or tablet); a video camera (standalone or integrated into another device such as a mobile phone or tablet); one or more sensors (e.g., gyro, accelerometer, global position system (GPS), image (e.g., camera or video camera), etc.) on a smartphone, surgical instrument, etc., in a skin patch (e.g., patches available from MC10 Inc. of Cambridge, Mass.), integrated into smart clothing, or in additional sensing or monitoring devices that can connect to the drug administration device 500 or the system 700 via wireless or wired connection, etc.; as well as any of a variety of known motion capture apps or motion capture software; etc. Further information regarding clinical outcomes and collecting patient data is provided in U.S. Pat. Pub. No. 2014/0081659 entitled "Systems and Method for Surgical and Interventional Planning, Support, Post-operative Follow-up, and Functional Recovery Tracking" published Mar. 20, 2014, which is hereby incorporated by reference in its entirety.

Once received by the system 700, the clinical outcome data can be aggregated with the data that is received from the drug administration device 500. The system 700 can analyze the aggregated data to identify trends and correlations which may exist between the drug and drug administration data received from the drug administration device 500 and the clinical outcome data. Additionally, the system 700 can receive data from one or more additional drug administration devices 500 and/or drug housing(s) 630 to identify trends and correlations among a patient population.

Such correlations can be determined, for example, by one or more data processing components, each associated with a data processor, of the system 700 which implement an artificial intelligence (AI) and machine learning system. Machine learning is an application of artificial intelligence that automates the development of a predictive model by using algorithms that iteratively learn patterns from data without explicit indication of the data patterns. Machine learning is commonly used in pattern recognition, computer vision, language processing and optical character recognition and enables the construction of algorithms that can accurately learn from data to predict model outputs thereby making data-driven predictions or decisions. Machine learning can be utilized to develop predictive models capable of generating clinical outcomes that are associated with one or more aspects of a patient's treatment, such as the patient's use of a drug administration device, a patient's conformance with a particular drug delivery schedule, surgery performed on the patient in which the drug administration device was used, etc.

The artificial intelligence and machine learning system configured within the system 700 can include one or more predictive models or algorithms which have been trained in a machine learning process or which implement a layered structure of deep learning algorithms, also known as an artificial neural network, which can continually analyze data and generate predations using the artificial neural network. The system 700 can perform untrained or deep learning to predict clinical outcomes based on the drug administration device usage and drug delivery data that is received from the drug administration device 500 (and/or additional drug administration device(s) 500 and/or drug housing(s) 630). In this way, features of drug administration device usage and/or drug delivery data can be used to accurately predict a specific clinical outcome. For example, the artificial neural network can process a diabetic patient's insulin injector usage data which indicated that the patient moderately adhered to a prescribed twice-daily insulin delivery timing and can determine a predicted clinical outcome indicating that the patient is unlikely to receive a protective reduction in elevated blood glucose levels. Further information regarding implementations of neural networks is provided in U.S. Pat. Pub. No. 2018/0189638 entitled "Hardware Accelerator Template Design Framework For Implementing Recurrent Neural Networks" published Jul. 5, 2018, which is hereby incorporated by reference in its entirety.

The artificial intelligence and machine learning system configured within the system 700 can include data processing components, each associated with a data processor, to perform trend analysis which can identify trends and variations in drug administration device usage and drug delivery data over time, in a surgical setting or otherwise. The trend analysis can include time-series data associated with how the self-reported or predicted clinical outcomes vary over time. The trend analyses can be compared to desired or predetermined patterns of drug administration device usage and drug delivery data as well as desired or predetermined patterns of clinical outcome data, including post-operative data. Such determinations can be made regarding the compliance of drug administration over time and the expected clinical outcome that may result based on the compliance determination. Evaluating compliance can thus allow monitoring and management of a patient's treatment, which can help the patient's doctor (and/or other medical professional) evaluate the patient's medical progress and/or can help determine whether and when modifications to the patient's treatment plan may be necessary, such as by adjusting the treatment plan (e.g., changing a dose size of the drug delivered from the drug administration device 500, changing a timing of doses delivered by the drug delivery device 500, changing dietary requirements, changing a frequency of doctor check-ups, etc.) or replacing the treatment plan (e.g., a treatment plan including use of the drug administration device 500 delivering a specific drug) with another treatment plan (e.g., a treatment that does not include any use of the drug administration device 500 and/or the specific drug). Further information regarding compliance determinations is provided in previously mentioned U.S. Pat. Pub. No. 2014/0081659 entitled "Systems And Methods For Surgical And Interventional Planning, Support, Post-Operative Follow-Up, And Functional Recovery Tracking" published Mar. 20, 2014.

For example, compliance data (e.g., data indicative of when a patient received doses from the drug administration device 500 in a surgical setting or otherwise) as compared to when the doses were prescribed per the patient's treatment plan) can be compared with historic compliance data for other patients who used the same type of drug administration device 500 and/or who received the same drug to help determine the effectiveness of the drug administration device 500 and/or the drug for the patient. The comparison can allow the system 700 to determine whether a patient and/or surgeon (and/or other medical professional) is adequately following the treatment plan or is lagging behind historical benchmarks achieved by other patients undergoing the treatment. The comparison can also allow the system 700 to evaluate treatment options for future patients because if a treatment is historically shown to be problematic for any one or more reasons (e.g., difficulty in achieving patient compliance, slow progress in addressing symptoms, expensive, lack of insurance payments, etc.) or shown to be particularly effective for any one or more reasons (e.g., drug dose sizes decline over time, use of the drug is reduced or is eventually eliminated, post-operative recovery time decreases if the drug is used during surgery, etc.), the system 700 can be more likely (for particularly effective treatments) or less likely (for problematic treatments) to recommend the treatment for future patients.

Because the system 700 can be configured to simultaneously and continuously receive information regarding multiple patients from multiple drug administration devices 500, the system 700 can repeatedly analyze received data to help determine efficacy of a particular patient's treatment plan that includes use of the same type of drug administration device 500 as other patients and/or use of the same drug as other patients. The system 700 can thus determine that a particular patient's treatment plan should be modified based on another set of patients' data indicating low or high effectiveness for that type of drug administration device 500 and/or that drug. In other words, the system 700 can learn from other patients' experiences that the present patient's treatment could benefit from a modification, e.g., use a different type of drug administration device 500 that has a lower failure rate and/or a higher compliance rate, prescribe a different drug, increase or decrease dose frequency, etc. The system 700 can be configured to suggest the modification of the patient's treatment plan to a user, e.g., the patient, the patient's surgeon (and/or other medical professional), the patient's care provider, etc., by providing an alert (e.g., email message, text message, instant message, phone call, etc.) to the user indicating that modification of the patient's treatment plan is recommended. The user can review the modification, e.g., by logging onto the system 700 and/or other computer system in communication therewith, and determine whether to modify the patient's treatment plan. Alternatively, the system 700 can be configured to automatically modify the patient's treatment plan and inform the user via an alert as to the modified treatment plan. Usually, a medical professional would review a modification to check its appropriateness for the particular patient before the system 700 automatically modifies the patient's treatment plan and informs the patient, and/or other users as appropriate, of the change.

The artificial intelligence and machine learning system configured within the system 700 can include data processing components, each associated with a data processor, to monitor the effectiveness of the drug that is delivered via the drug administration device 500 (and/or additional drug administration device(s) 500 and/or drug housing(s) 630). In at least some embodiments, the system 700 can be configured to process the drug administration device usage and drug delivery data that has been aggregated with the clinical outcome data to determine how well the drug provides a therapeutic benefit and if the drug causes the patient to experience any side effects which may be reported via the clinical outcome data, including post-operative data. For example, the system 700 may determine a correlation between a particular drug (or a particular drug delivery schedule) and self-reported and/or sensed symptoms of nausea. The system 700 may further process data associated with an individual patient's medical history to determine a suitable dosage or delivery schedule which is less likely to cause nausea. In this way, new drugs or drug delivery regimens can be determined which produce a desired clinical outcome for a patient population. For another example, the system 700 may determine that patients receiving a different drug than the drug delivered to the patient did not experience a side effect experience by the patient receiving the drug and/or experienced the side effect less severely than the patient receiving the drug. The system 700 may thus determine that the drug received by the other patients would be a good alternative to suggest for the patient receiving the drug in an effort to stop the patient from experiencing the side effect or to reduce the side effect's severity.

In some embodiments, the system 700 can be configured to electronically transmit an instruction, which is based on the system's analysis of previously received data, to the drug administration device 500. The drug administration device 500 can be configured to execute the received instruction on board the drug administration device 500 to change at least one aspect of the device's/housing's functionality. The system 700 can thus be configured to remotely control the drug administration device 500.

For example, the instruction from the system 700 can include a request for the drug administration device 500 to alter the predetermined schedule at which data sensed by the one or more sensors is transmitted to the system 700 in embodiments in which the predetermined schedule is programmed into the memory 97 of the drug administration device 500. A doctor or other medical professional reviewing information about the drug administration device 500 gathered by the system 700 may desire more frequently sensed information to facilitate the doctor's or other medical professional's analysis of the patient's treatment plan, including during execution thereof such as during performance of a surgical procedure, and thus input a request to the system 700 for the system 700 to update the drug administration device's stored predetermined schedule.

For another example, the instruction from the system 700 can include a request for the drug administration device 500 to alter a function of drug delivery, such as the delivery schedule of the drug, a rate of drug injection, and a dosage of the delivered doses. A doctor or other medical professional reviewing information about the drug administration device 500 gathered by the system 700 may desire the altered function of drug delivery based on the information review. More particularly, an algorithm stored in the memory 97 of the drug administration device 500 can be executable on board by the processor 96 to administer a dose of the drug to a patient. The algorithm is stored in the form of one or more sets of pluralities of data points defining and/or representing instructions, notifications, signals, etc. to control functions of the device and administration of the drug. Data received by the drug administration device 500, e.g., as pluralities of data points via a communications interface thereof, is used, e.g., by the processor 96, to change at least one variable parameter of the algorithm based on the received instruction identifying the parameter to change and the parameter's updated value. The at least one variable parameter is among the algorithm's data points, e.g., are included in instructions for drug delivery, and are thus each able to be changed by changing one or more of the stored pluralities of data points of the algorithm. After the at least one variable parameter has been changed, subsequent execution of the algorithm administers another dose of the drug according to the changed algorithm. As such, drug delivery over time can be remotely managed for a patient, e.g., by a medical professional providing input for the drug delivery change to the system 700, to increase the beneficial results of the drug. Changing the at least one variable parameter and/or administration of the one or more doses themselves is automated to improve patient outcomes. Thus, the system 700 can be configured to facilitate personalized medicine based on the patient to provide a smart system for drug delivery.

The artificial intelligence and machine learning system configured within the system 700 can include data processing components configured to receive financial data that is associated with the costs of providing medical care to a patient. The received financial data can be used in a cost-benefit analysis for various drugs or therapeutic regimens which may be prescribed for a particular patient. The financial data includes payer, insurance, and/or hospital cost data, which when analyzed in regard to drug administration device usage and drug delivery data and the clinical outcome data, may provide insights as to lower cost alternatives of drugs which yield substantially the same clinical outcomes as the drug. For example, a particular drug may be associated with a lower insurance reimbursement rate and/or a lower hospital cost than another drug, where each of the drugs were used to treat the same medical issue (e.g., blood pressure, asthma, pain, etc.) and each had substantially similar clinical outcomes associated therewith. The drug with the higher insurance reimbursement rate and/or higher hospital cost rate may therefore be identified by the system 700 as a more financially sound option for a patient currently receiving (or planned to receive) the other drug as part of the patient's treatment plan. A person skilled in the art will appreciate that clinical outcomes may not be precisely the same but nevertheless be considered to be substantially the same as one another for any number of reasons, such as due to statistical standard deviation.

The system 700 can be configured to use the aggregated data to perform predictive modeling of drug delivery conformance and resulting clinical outcomes for a particular patient based on hypothetical parameters that can be provided to the system 700 by the patient's doctor and/or other care provider. The artificial intelligence and machine learning system configured within the system 700 can include data processing components configured to implement a machine learning process trained to generate a predictive model capable of receiving input parameters associated with the drug administration device usage or drug delivery data and to predict clinical outcomes based on the inputs. Once trained during a training phase of the machine learning process, the predictive model can be deployed as a trained prediction model within the system 700 and can be accessed via a user interface such as a web-based application configured on a web browser of a computer system at a medical facility 706 or via a user interface such as an app configured on a smart phone or other mobile computing device at a mobile location 710. The interface to the trained prediction model can allow a user to input data parameters for a particular patient associated with a particular treatment. The input parameters can include any one or more of, for example, parameters related to a drug delivery schedule, a drug dosage, a drug type, a drug administration device type, and the like. The trained prediction model can process the inputs and provide the user with a predicted clinical outcome, a predicted side effect, and/or other predicted behavioral or physiological changes that are predicted to become symptomatic for the particular patient based on the inputs. In this way, the system 700 may improve the ability of the physician or other care provider to assess various drug delivery schedules and alternate configurations of the drug administration device 500 in a controlled, low-risk manner before administering a new treatment regimen to the patient.

The system 700 can be configured to receive data transmitted from the drug administration device 500 and to process the data in regard to data and metadata that is associated with a medical professional's summary of a patient's treatment over time as recorded in the patient's medical history file. The system 700 can be configured to receive the physician summary data or metadata from a hospital information system as the physician summary data is entered into the patient's medical history file, such as from a cloud-based system such as the cloud 1004 of FIG. 9. The system 700 can be configured to analyze the physician summary data with respect to the data transmitted from the drug administration device 500 so that adherence to a prescribed drug regimen or therapeutic treatment can be determined in real-time or in near real-time. In this way, adherence trend analysis and reporting can be performed more rapidly than in systems which may not receive drug administration device usage and drug delivery data or may not integrate medical professional summary data as configured in the system 700.

Receiving physician summary data as it is recorded in the patient's medical history file allows the system 700 to immediately generate notifications as soon as non-compliant conditions are determined, such as a patient's allergy to a drug, adverse drug interactions, etc. The notifications can be generated as alerts or alarms which can be transmitted to one or more computer systems to inform a patient, the patient's doctor, and/or other appropriate medical professional that the patient is experiencing a non-compliance issue or other medical situation which requires immediate attention. The notification may enable the doctor and/or appropriate medical professional to rapidly instigate action to alleviate or reduce the non-compliant situation.

In at least some embodiments, the system 700 can include one or more data filters which can be applied to the physician summary data that has been aggregated with the data transmitted from the drug administration device 500. The data filters can include, for example, filters to parse the aggregated data on the basis of geographic region or ethnicity so that significant trends associated with patients included in the filtered data can be determined.

The system 700 can be configured to receive data transmitted from the drug administration device 500, and to process the data automatically and in real-time or near real-time to determine a complaint associated with the drug administration device 500. The system 700 can process received device usage data to determine a malfunction of the drug administration device 500 and, based on the malfunction, can generate a complaint. For example, device usage data received from the drug administration device 100 of FIG. 1 can indicate to the system 700 that the discharge nozzle 122 is failing to extend out of the housing 130 during an injection sequence and as a result is failing to deliver the drug to the patient. The complaint can be generated as an alert or an alarm that is transmitted to one or more computer systems to inform the patient, the patient's doctor and/or other appropriate medical professional(s) of the device malfunction. Based on the generated complaint, the system 700 can further notify a manufacturer of the drug administration device of the malfunction of the drug administration device and request a new drug administration device be configured and provided directly to the patient and/or to another location. Embodiments of interfaces that can be used to provide an alert or alarm are further described in U.S. Pat. Pub. No. 2008/0154177 entitled "System And Method For Remote Monitoring And/Or Management Of Infusion Therapies" published Jun. 26, 2008, which is hereby incorporated by reference in its entirety.

The system 700 can be configured to generate a malfunction report that is pre-populated with patient-specific device data describing the configuration of the malfunctioning drug administration device. In this way, the system 700 can assist diagnosing quality assurance issues for the drug administration device while ensuring that the patient is able to maintain their prescribed drug delivery schedule using a functioning drug administration device which may be provided as a replacement to the malfunctioning drug administration device.

The system 700 can be configured to respond to requests for additional data that are received from a remote location, such as the mobile location 710 of FIG. 7. A user at the remote location, e.g., a physician or other medical professional providing care to the patient, may desire the additional data for any of a variety of reasons, such as wanting the system 700 to receive and analyze more current information from a single drug administration device 500 or a plurality of drug administration devices 500 to better understand a particular trend, a previous cost conclusion, or other prior analytical output of the system 700, to trigger gathering of a particular type of data not previously received by the system 700 so this type of data can be included in the system's analysis, to help determine if an identified malfunction with a particular drug administration device 500 is unique to that device 500 or may be a problem with a group of related drug administration device 500, etc. For example, the request for additional data can include a request for data associated with a particular patient's drug administration device 500 or the configuration of the patient's drug administration device 500, such as the specific drug that is contained within the drug administration device 500 or specifications of a specific component within the drug administration device 500. For example, the request for additional data can include a request for data associated with a specific class of drug administration devices, including the patient's drug administration device 500, such as device model numbers, manufacturing lot numbers, and data identifying or otherwise associated with the patient population to whom the drug administration device 500 has been prescribed for use. For yet another example, the request for additional data can include a request for data that is associated with a specific drug which may be administered by the drug administration device 500 or a class of drug administration devices that includes the patient's drug administration device 500, such as the drug formulation, dosing data, type or class of drugs, as well as characteristics associated with the administration method of the drug administration device 500 which, for example, can include the viscosity of the administered drug in the case of injector-type devices.

The system 700 can be configured to aggregate data that is received from the drug administration device 500 with clinical outcome data to detect irregular treatment conditions for a particular treatment that has been prescribed to be performed using a particular configuration of the drug administration device 500. For example, the irregular treatment conditions include irregular dosage events, un-prescribed dosage timing intervals, and indicators of negative clinical outcomes, which can include post-operative outcomes as mentioned above. The system 700 can utilize the aggregated data to identify when the particular treatment is being performed outside of the prescribed or expected treatment parameters and can generate suggestions which are likely to improve the clinical outcome experienced by the patient. The generated suggestions can include action(s) to be performed when the system 700 determines that the irregular treatment conditions are associated with better than expected clinical outcomes. For example, if the system 700 determines that a patient's irregular treatment conditions result in an improved clinical outcome, the system 700 can mark the improved clinical outcome in a database and can initiate a search of data that may support or refute the unexpected improvement in the clinical outcome. The system 700 can be configured to analyze the search results, for example using natural language processing. If the system 700 determines that the irregular treatment conditions support the improved clinical outcome, the system 700 can forward the search results to pre-determined personnel for further consideration to include aspects of the irregular treatment conditions as a modification to the particular treatment or the particular configuration of the drug administration device 500.

When the system 700 determines that the irregular treatment conditions are associated with worse than expected clinical outcomes, the system's generated suggestions can include action(s) to be performed. For example, if the system 700 determines that a patient's irregular treatment conditions result in a worse or negative clinical outcome, the system 700 can generate a notification to the patient and/or to the patient's medical professional(s) informing each of them that an improved treatment or an improved configuration of the drug administration device 500 is available which may result in expected or improved clinical outcomes. For example, the notification may suggest to change the dosage intervals from, e.g., once per day to twice per day. Additionally, the notification can include various means or affordances to facilitate a conversation between the patient and his/her care provider in regard to the irregular treatment conditions and the resulting negative clinical outcomes. The notification to the patient's medical care professional can include details of the originally prescribed treatment and the corresponding configuration of the drug administration device 500 for the particular treatment. The notification to the patient's medical care professional can also include the expected clinical outcomes for the particular treatment that was originally prescribed.

Data Security

Data communicated from a drug administration device to a computer system, from a computer system to a drug administration device, or from one computer system to another computer system can be configured to be communicated in a secure and anonymized manner. In this way, data related to a patient's drug administration device, a drug dispensable or dispensed from a patient's drug administration device, sensed patient data, and/or a patient's medical history or record can be transmitted between devices/systems without any identifying patient information that would compromise the patient's privacy if the data was intercepted by an unauthorized party. A remembered link can be established between the transmitting party and the receiving party to facilitate this secure, anonymous communication of data. As discussed above, the transmitting and receiving parties can be any of the drug administration devices described herein such as those of FIGS. 1-5, any of the drug housings 30, 630 of FIGS. 5 and 6, the packaging 35 of FIG. 5, a sensor, etc. or any of the computer systems described herein such as those of any of FIGS. 7, 9, and 10. In an exemplary embodiment the remembered link includes an established key stored at each of the transmitting party and the receiving party that is unique to the transmitting party and the receiving party, thereby allowing the receiving party to receive anonymous data from the transmitting party but, using the key, be able to accurately identify the data as being from that particular transmitting party and, therefore, as being associated with the particular patient associated with that particular party as previously programmed at the receiving party or available thereto from another computer system. The receiving party may therefore aggregate data received from the transmitting party and related to a drug administration device, a drug deliverable/delivered from the drug administration device, and/or a patient for evaluation of the patient's condition and treatment and/or for evaluation of the efficacy of the drug administration device and/or the drug. The evaluation can be manually performed by a medical professional or can be automated by a computer system, as discussed above.

The identification of data as being associated with a particular patient does not necessarily require the identification of the full details of the patient. At a basic level identification of the data as associated with a particular patient can maintain the privacy of the patient so they cannot be uniquely identified but still allow the aggregation of multiple bits of data that are associated with one patient. This enables the collection of anonymous data that can be used for assessing correlations and trends associated with drug administration or other conditions encountered by the patients. This anonymous data can also be used in place of a control group as part of a clinical trial. The assessment of correlations and trends can be used for generation of evidence and support for new clinical treatment standards, e.g., new procedures changes, new device changes, new drug usage, etc.

A receiving party can be configured to establish a unique key with each of a plurality of transmitting parties. For example, a computer system can be configured to establish a unique key with each of a plurality of drug administration devices, drug housings, packagings, and/or sensors to allow the computer system to aggregate data from each of the different sources, thereby allowing for data analysis between different patients and/or data analysis between different devices/housings/packagings. Such analysis may be useful for any number of reasons, such as allowing for evaluation of treatments of different patients for optimal clinical outcomes, allowing for evaluation of patients' compliance with their individual medical treatment plans, and/or allowing an insurance company to more effectively correlate drug usage and drug cost. For another example, a computer system can be configured to establish a unique key with each of a plurality of other computer systems, thereby allowing for data analysis between different patients and/or data analysis between different devices/housings/packagings.

The remembered link uses encryption to achieve secure, private, and anonymous data communication. In an exemplary implementation a computer system includes a server configured with a key-based security system, such as a public key/private key cryptographic system, to allow for data encryption and decryption. The server can be a remotely located server relative to the drug administration device, housing, or other device in communication therewith or can be local to the drug administration device, such as a surgical hub located locally to a drug administration device in use during performance of a surgical procedure. The server thus includes a memory, such as memory 897, and/or a database, such as additional storage 810, configured to store public and private keys for devices configured to communicate with the system. Public and private keys can be generated using cryptographic algorithms by the server. Keys can be used to encrypt data for transmission and to decrypt encrypted data received from a different computing system and/or from a drug administration device. In such systems, a public key associated with the intended receiver of the data can be utilized to encrypt data, however, only the recipient's private key can be used to decrypt the encrypted data. In at least some embodiments, the server includes a cryptographic system such as a public key infrastructure (PKI), in which one or more third parties, known as "certificate authorities," can certify ownership of the public and private key pairs. Examples of key-based security systems include the Diffie-Hellman key exchange protocol, the Digital Signature Standard (DSS) protocol, password-authenticated key agreement protocols, the Rivest-Shamir-Adelman (RSA) encryption algorithm, the Cramer-Shoup cryptosystem, and the YAK authenticated key agreement protocol.

More particularly, encryption is achieved with algorithms that use a key to encrypt and decrypt messages by turning text or other data into an unrecognizable digital form and then by restoring it to its original form. The longer the key, the more computing is required to crack the code. Computer keys are made of bits of information of various length. For example, an 8-bit key has 256 (2 to the eighth power) possible values. For another example, a 56-bit key creates 72 quadrillion possible combinations. If the key is 128 bits long, or the equivalent of a 16-character message on a personal computer, a brute-force attack would be 4.7 sextillion (4,700,000,000,000,000,000,000) times more difficult than cracking a 56-bit key. With encryption, unauthorized use of the data is generally prevented, even in the rare event that the data transmitted is intercepted by an unauthorized party.

A unique identification (ID) number or code is registered and stored in the device's memory, e.g., memory 97 of the device 500 of FIG. 5, etc., such as during the manufacturing process before any use of the device. The ID number/code is unique to the device, although the ID number/code can include additional identifying information, such as a model or model family number or code, that is common to a plurality of devices and that may be useful in analyzing trends among a plurality of related devices. In an exemplary embodiment, the ID number is transmitted to the computer system with the drug administration device, drug, and/or sensor data to facilitate the computer system's identification of the data as coming from that particular drug administration device. The computer system can perform this identification in any number of ways, such as by looking up the ID number/code in a lookup table stored at the computer system that correlates ID numbers/codes of devices that may communicate with the drug administration device to particular keys so the computer system can identify which previously generated key to use to decrypt the data received from the drug administration device. The lookup table can also correlate the ID numbers/codes to particular drug administration devices and/or to particular patients associated with the particular drug administration devices. The ID number/code may not be encrypted in the data transmitted from the drug administration device to the computer system to allow the computer system to read the ID number/code and identify the correct key to use for decryption.

The key generated at the computer system for communication with a particular party is shared with the party and stored at the party in a memory thereof, as discussed above. In some embodiments, instead of the computer system generating the key and transmitting the key to the party for storage at the party, the party can perform the key generation and transmit the key to the computer system for storage thereat. A server will typically have greater processing capability than a drug administration device, so in an exemplary embodiment for communication between a server and a drug administration device, key generation occurs at a server instead of at a drug administration device. In other embodiments, using certain key generation protocols that will be appreciated by a person skilled in the art, each of a computer system and a drug administration device participate in key generation such that a key is transmitted to one or the other of the computer system and the drug administration device, which may help improve security since avoiding key transmission prevents the key from being intercepted by an unauthorized party.

Using the universal drug administration device 500 of FIG. 5 and the computer system 700 of FIG. 7 by way of example, the drug administration device 500 can utilize the key-based security system to manage data storage and data transmission operations between the drug administration device 500 and the system 700. A key can be established between the drug administration device 500 and the computer system 700 using any of a variety of key establishment protocols. The key can be stored in the memory 97 of the device 500 and stored in a memory of the computer system 700 to allow the drug administration device 500 to encrypt data using the key and to transmit the encrypted data to the computer system 700 securely and in an anonymous manner that does not identify the drug administration device 500 or the patient associated therewith. The device's memory 97 can also store therein a unique ID number/code for the drug administration device 500. The drug administration device's processor 96 can be configured to use the key in encrypting data indicative of information sensed by any one or more of the device's sensors 92, 94, 98 and/or any other data communicated from the drug administration device 500 to the system 700. The data can include metadata for the sensed information, such as time and date the data was collected. The drug administration device's processor 96 can be configured to cause the encrypted data to be transmitted wirelessly to the system 700 via the communications interface 99 of the drug administration device 500. The computer system 700 can then receive the data via its communications interface, identify from the received data the correct key stored in its memory to use in decrypting the received data, and then decrypt the received data using the identified, stored key. In this way, the computer system 700 can be configured to remove the anonymized aspect of the data to allow identification of the drug administration device 500 and the patient associated with the data since the key is previously known by the computer system 700 to be associated with that particular drug administration device 500 and patient. As noted elsewhere herein, the level of anonymity removal may maintain a degree of privacy of the patient when the precise identity of the patient is not required. Conversely, an unauthorized party that intercepts the data transmitted by the drug administration device 500 would not be able to remove the anonymized aspect of the data and, therefore, even in the event that interception occurs, the patient's privacy is maintained. The drug administration drug administration device 500 can utilize the generated key to encrypt all data that is transmitted from the drug administration device 500 to the system 700. The computer system 700 can also utilize the generated key stored thereat to encrypt any data transmitted therefrom to the drug administration device 500, with the drug administration device 500 able to decrypt that information using its stored key. Data transmitted from the system 700 to the drug administration device 500 can include, for example, a request for the drug administration device 500 to transmit sensed information to the system 700 in embodiments in which the drug administration device 500 is not configured to automatically transmit sensed information to the system 700.

Figure 11:
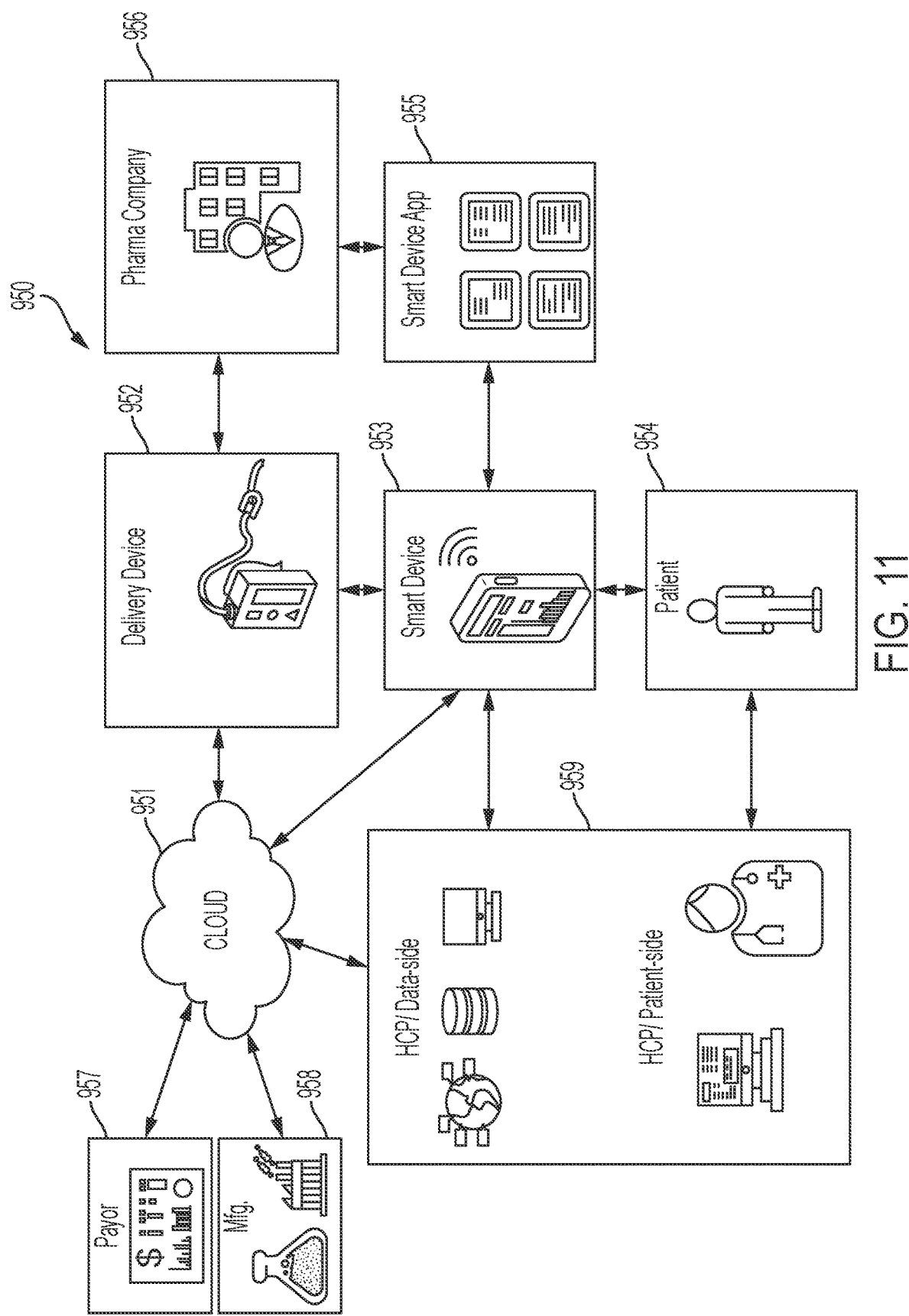
FIG. 11 is a schematic view of one embodiment of a drug administration system including a cloud-based system and a drug administration device.

FIG. 11 illustrates one embodiment of a drug administration system 950 including a cloud-based system 951 configured to communicate with one or more drug administration devices in a secure and anonymized manner using a key-based security system. The drug administration system 950 in this illustrated embodiment includes a drug administration device 952 configured to communicate with the cloud-based system 951, a smart mobile device 953 configured to communicate with the cloud-based system 951 and the drug administration device 952, a patient 954 configured to have a drug delivered thereto from the drug administration device 952 and to interact with the mobile smart device 953, one or more apps 955 installed on the smart device 953 and configured to facilitate a user's interaction with the smart device 953 as related to the drug administration device 952, a pharmaceutical company computer system 956 for a pharmaceutical company associated with the drug and configured to communicate electronically with the one or more apps 955 (e.g., to provide software updates thereto, to push informational notifications thereto to provide to the patient 954, etc.) and with the drug administration device 952 (e.g., to push informational notifications thereto related to the drug to provide to the patient 954 via a user interface of the device 952, etc.), a payor database 957 configured to store payor data related to the patient 954 and to be accessible to the cloud-based system 951, a manufacturing database 958 configured to store drug data related to manufacturing of the drug and to be accessible to the cloud computing system 951, and a patient database 959 configured to store patient data related to the patient 954 and to be accessible to the cloud-based system 951, the patient 954, and the smart device 953. The drug administration device 952 can be any of the drug administration devices discussed above. The patient database 959 includes data-side health care provider (HCP) data regarding the patient 954 that is configured to be accessible to the cloud-based system 951. The patient database 959 also includes patient-side HCP data regarding the patient 954 that is configured to be accessible to the patient 954, such as via the smart device 953 under patient control. A surgical hub can include the patient database 959. As discussed above, the drug administration device 952 can be configured to communicate with the surgical hub, which can be configured to communicate with the cloud-based system 951.

The drug administration device 952 can be configured to communicate with the cloud-based system 951 and/or the surgical hub using a security system, such as a key-based security system. A key can be established between the drug administration device 952 and the cloud-based system 951 using any of a variety of key establishment protocols. The key can be stored in a memory of the device 952 and stored in a memory of the cloud-based system 951 to allow the drug administration device 952 to encrypt data using the key and to transmit the encrypted data to the cloud-based system 951 securely and in an anonymous manner that does not identify the drug administration device 952 or the patient 954 associated therewith. The drug administration device's memory can also store therein a unique ID number/code for the drug administration device 952. The drug administration device's processor can be configured to use the key in encrypting data indicative of information sensed by any one or more of the drug administration device's one or more sensors (and/or other sensor(s)). Alternatively, the drug administration device 952 can be the sensor itself and so be configured to use the key in encrypting data indicative of information sensed. The data can include metadata for the sensed information, such as time and date the data was collected. The drug administration device's processor can be configured to cause the encrypted data to be transmitted wirelessly to the cloud-based system 951 via the drug administration device's communications interface. The cloud-based system 951 can then receive the data via its communications interface, identify from the received data the correct key stored in its memory to use in decrypting the received data, and then decrypt the received data using the identified, stored key. In this way, the cloud-based system 951 can be configured to remove the anonymized aspect of the data to allow identification of the drug administration device 952 and the patient 954 associated with the data since the key is previously known by the cloud-based system 951 to be associated with that particular drug administration device 952 and patient 954. Conversely, an unauthorized party that intercepts the data transmitted by the drug administration device 952 would not be able to remove the anonymized aspect of the data and, therefore, even in the event that interception occurs, the patient's privacy is maintained. The drug administration device 952 can utilize the generated key to encrypt all data that is transmitted from the device 952 to the cloud-based system 951. The cloud-based system 951 can also utilize the generated key stored thereat to encrypt any data transmitted therefrom to the drug administration device 952, with the drug administration device 952 being able to decrypt that information using its stored key. Data transmitted from the cloud-based system 951 to the drug administration device 952 can include, for example, a request for the device 952 to transmit sensed information to the cloud-based system 951 in embodiments in which the device 952 is not configured to automatically transmit sensed information to the cloud-based system 951. In at least some embodiments, a key can be similarly established and used between the cloud-based system 951 and each of any one or more of the other computer systems 953, 957, 958, 959 in the system 950 with which the cloud-based system 951 is configured to communicate, including a surgical hub.

Figure 12:
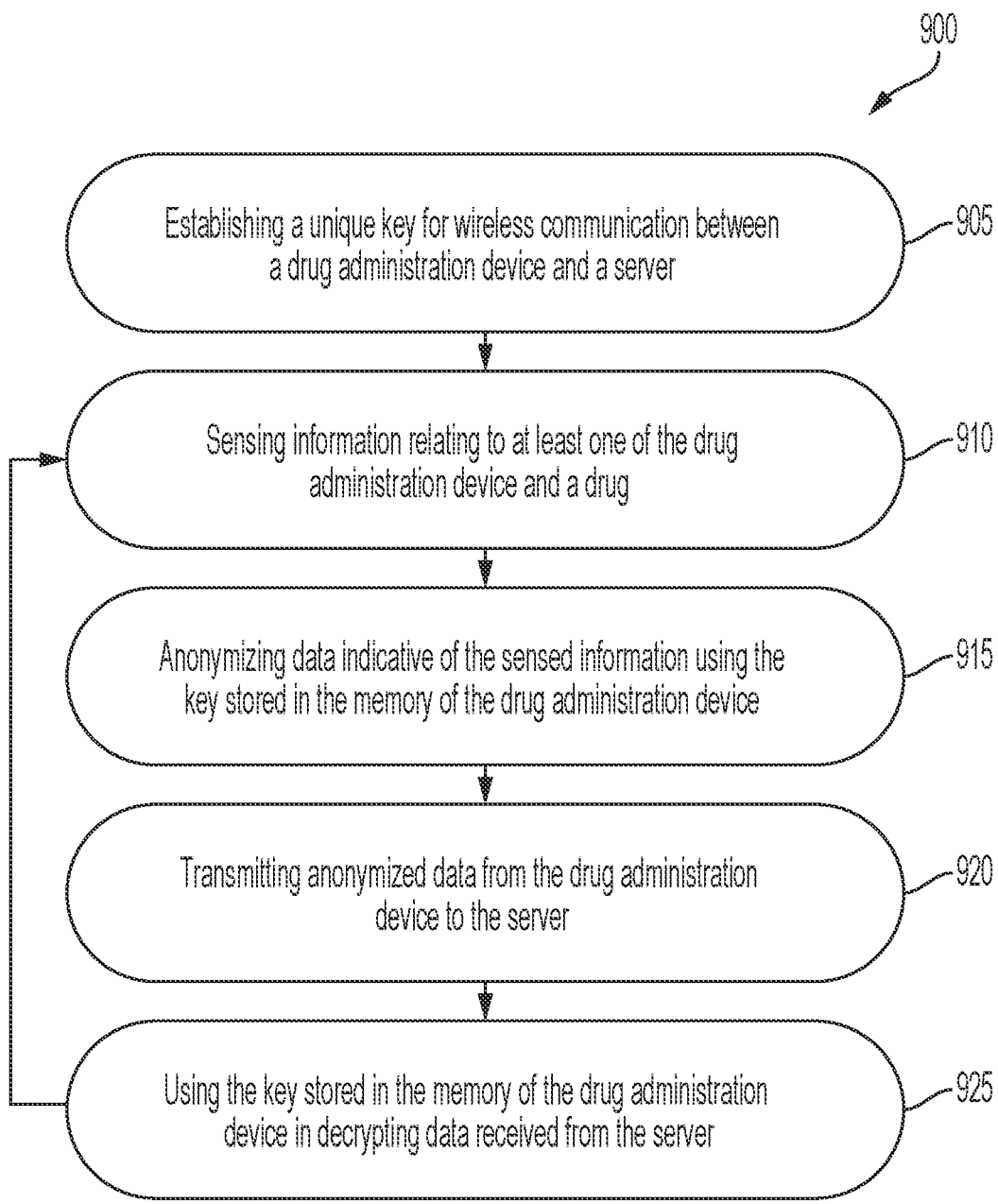
FIG. 12 is a flowchart illustrating one embodiment of a method for administering a drug using a key-based security system.

FIG. 12 illustrates one embodiment of a method 900 using a key-based security system. The method 900 is described with respect to the drug administration devices 500 of FIG. 5 and the system 700 of FIG. 7 for ease of explanation, but other drug administration devices and computer systems can be similarly implemented as discussed above. The key-based system is used to encrypt and decrypt data that is transmitted and received between the drug administration device 500 and the system 700 so that data can be passed in a secure, private, anonymized manner.

The key-based security system establishes 905 a unique key for wireless communications between the drug administration device 500 and the system 700 located remotely from the drug administration device 500, although as mentioned above a key-based security system can be used for wireless communications between a drug administration device and a local server such as a surgical hub. In at least some embodiments, a server configured within the system 700 implements the key-based security system. The unique key is stored in a memory of the server, as well as in an additional storage that may be configured with the system 700. The system 700 can transmit the key to the drug administration device 500 for storage in the memory 97 thereof, or, as discussed above, the drug administration device 500 can be configured to generate its own key of a key pair to be used in the key-based security system.

The drug administration device 500 senses 910, e.g., using one or more of the sensors 92, 94, 98, information relating to at least one of the drug administration device 500 and the drug to be dispensed therefrom. The sensed information can include, for example, data associated with the dosage amounts and the delivery schedule of the drug to be administered via the drug administration device 500.

The processor 96 of the drug administration device 500 uses the generated key stored in the memory 97 to encrypt and anonymize 915 data indicative of the sensed information. The processor 96 anonymizes and encrypts the data prior to transmission 920 of the data to the system 700 such that when transmitted, the data is transmitted in a secure, encrypted manner. The transmission in operation 920 also includes the device's unique ID number/code to facilitate the computer system's decryption of the data received from the drug administration device 500.

If the drug administration device 500 receives 925 encrypted data from the system 700, the drug administration device 500 uses the key stored in memory 97 to decrypt the data that is received.

In relation to a sensor being configured to sense information relating to a physiological parameter of a patient, whether the drug administration device includes the sensor or the sensor is external to and separate from the drug administration device, the sensor can be configured to obtain information relating to the physiological parameter on a regular basis, e.g., at least once every twenty-four hours, once every twelve hours, once every three hours, once every hour, once every thirty minutes or once every ten minutes, etc. This can be chosen in line with the frequency of data required. This data can then be communicated anonymously to a server, as described herein, at a corresponding frequency or a lower frequency as required. The sensor may therefore enable the collection of data in an anonymous manner such that is can be utilized without risk of identifying the original patient and thus assist with patient acceptance relating to the collection of their data.

As discussed above, a single patient can have a plurality of sensors for measuring different parameters, which can be further physiological parameters. These sensors can all be associated with the same patient within the system allowing the aggregation of data on the server in relation to this patient.

Data associated with a single patient, beyond the physiological information obtained by the sensor, can also be obtained. For example, a drug administration device associated with the patient can also communicate data relating to the patient, as described herein, and be aggregated with the physiological information on the server to give an indication of physiological response to certain drug administration device performance.

A plurality of patients can each have at least one sensor for measuring a physiological parameter. The sensors are each associated with their respective patient within the system allowing the storing of data for each patient. This allows the collection of many data points across a range of patients which may assist in finding trends and correlations. In particular, each of the plurality of patients can have a plurality of sensors contributing to more data points assisting further analysis of observed outcomes. Each of the plurality of patients can have a drug administration device associated with them providing further data to the server.

Communication of sensor data can be repeated at a periodic rate of, for example, once every twenty-four hours. The periodic measurement can be repeated for a duration of at least twenty-four hours such as forty-eight hours, seven days, fourteen day, thirty days, ninety days, one hundred twenty days, one hundred eighty days, three hundred sixty-five days, etc. In this way, it is possible to complete short term tests over hours and days, but also accumulate more data over a longer period of time to enable highly accurate testing. For example, where the monitored physiological parameters include blood glucose level and nutritional intake such as carbohydrate intake and body weight, the steps can be repeated for duration of three hundred sixty-five days to provide a highly accurate long term glucose test that would be otherwise unachievable using traditional methods. This may better inform real world treatment algorithms.

Figure 13:
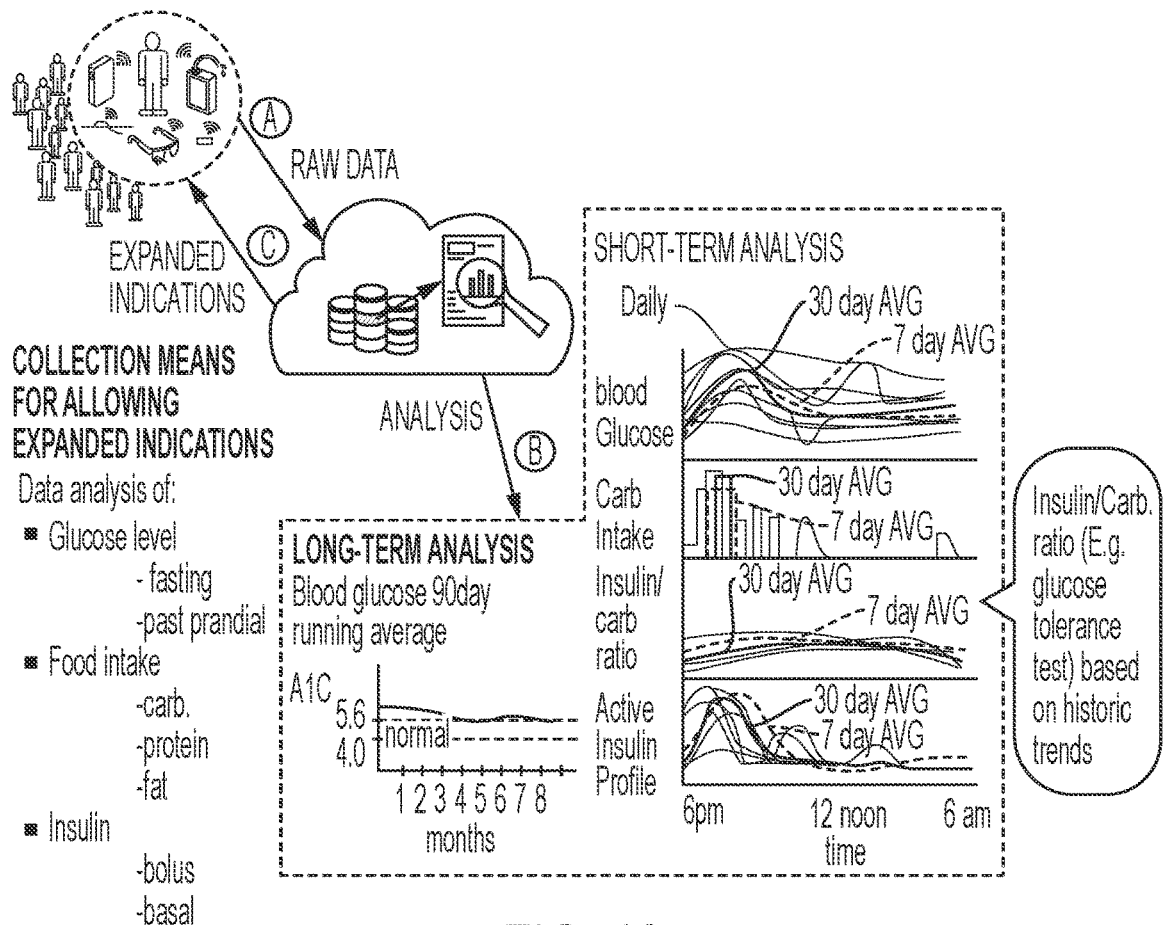
FIG. 13 is a schematic view of one embodiment of a system utilizing a sensor.

FIG. 13 shows one embodiment of a system configured to accumulate data associated with one patient of a plurality of patients. The system can identify that one patient and so extract recorded data associated with this patient. In this embodiment, the extracted data are blood glucose, carbohydrate intake, and patient response to insulin administration. These data can be analyzed to provide a ratio of response to insulin administration/carb ratio over a thirty day average and a seven day average in the short term. The sensed data also provides an average blood glucose level over a ninety day average for long term analysis. The ability to extract such data can allow trends to be established for individual patient circumstances. Such patient data can be combined with patients of a similar situation to build up a picture of trends across any particular part of the population. This may benefit optimization of dosing schemes for new patients who do not have any historical data.

Figure 14:
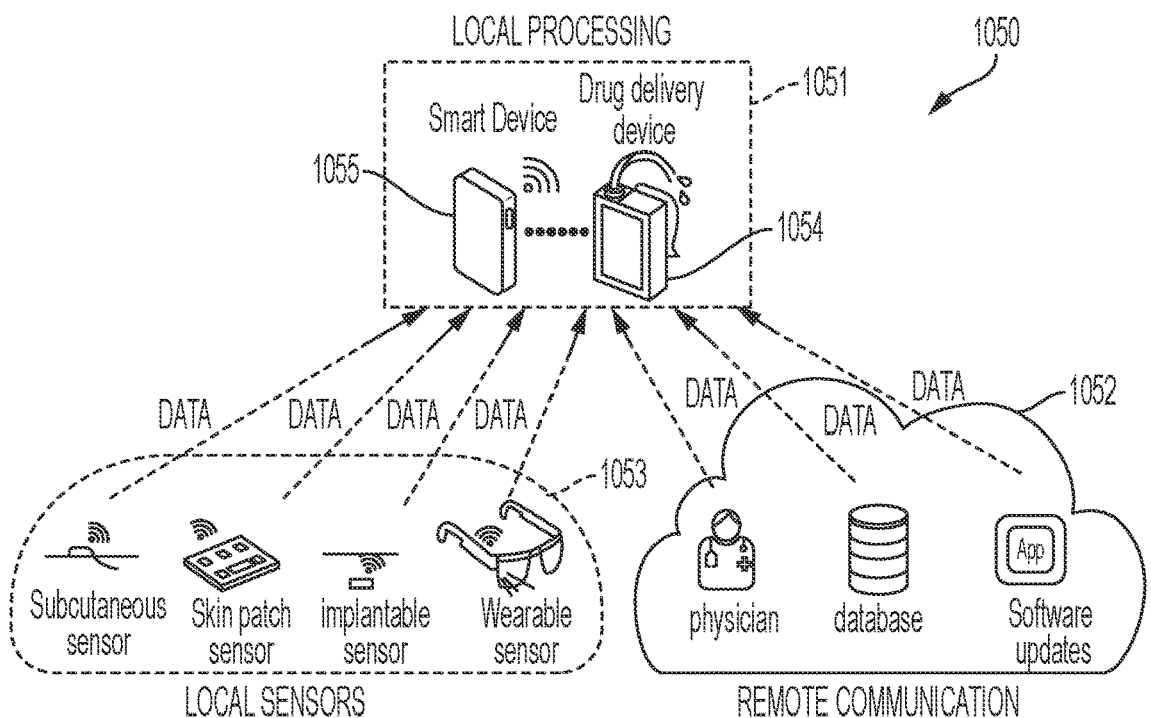
FIG. 14 is a schematic view of one embodiment of a drug administration system including a drug administration device and a remote computer system.

FIG. 14 shows another embodiment of a drug administration system 1050 configured to accumulate data associated with one patient of a plurality of patients. In this illustrated embodiment, the drug administration system 1050 includes a local processing system 1051, a remotely located computer system 1052 (remotely located relative to the local processing system 1051) configured to communicate with the local processing system 1051, and local sensors 1053 (local to a patient associated with the local processing system 1051) each configured to communicate with the local processing system 1051.

The local processing system 1051 includes a drug administration device 1054 and a mobile smart device 1055 configured to electronically communicate with the drug administration device 1054. A surgical hub can be used instead of or in additional to the mobile smart device.

The smart device 1055 and/or the drug administration device 1054 can be configured to receive data from the sensors 1053 and show information related thereto on a user interface thereof. In this illustrated embodiment, the sensors 1053 include a subcutaneous sensor, a skin patch sensor, an implantable sensor, and a wearable sensor. The received sensor data can be transmitted to the remote system 1052 for analysis, which can, for example, trigger updating of an algorithm for dose delivery, as discussed herein. The smart device 1055 and/or the drug administration device 1054 can each include one or more on-board sensors in addition to, or in alternative to, any or all the off-board sensors 1053. The on-board sensor data can be transmitted to the remote system 1052 for analysis that can, for example, trigger updating of the algorithm, as discussed herein.

A memory of the drug administration device 1054 can have stored therein the algorithm, and the drug administration device's processor can be configured to execute the algorithm to control delivery of a dose of the drug dispensed by the drug administration device's dispensing mechanism, as discussed herein. The drug administration device's communications interface can be configured to receive an instruction from a communications interface of the remote computer system 1052 requesting a change to at least one variable parameter of the stored algorithm. In response to the instruction, the drug administration device's processor can be configured to change at least one variable parameter of the algorithm as requested such that a dose delivered subsequent to the changing of the at least one variable parameter will be controlled by execution of the changed algorithm. Alternatively, a memory of the smart device 1055 can have the algorithm stored therein, with the remote computer system 1052 instead communicating with the smart device 1055 to control updating of the algorithm, and can be configured to execute the algorithm and thereby cause a command for drug delivery to be provided to the drug administration device 1054.

Feedback/Notifications

Feedback/notifications can be provided to a user via a drug administration device and/or a computer system based on some aspect of data related to the patient's drug administration device, such as some aspect of the data exceeding a threshold or based on a rule. In at least some embodiments, feedback/notifications can be provided in a hierarchical manner based on the criticality of certain individual or combined data parameters. For example, when data associated with the operation of the patient's drug administration device, such as reduced needle penetration depth, is combined with a particular physiological condition sensed via at least one sensor of the drug administration device, such as elevated blood sugar levels, the drug administration device's user interface and/or other user interface, e.g., surgical hub display or other interface, can be configured to notify a user to take action to correct a malfunctioning drug administration device which may be causing elevated blood sugar levels. The feedback/notification can identify the corrective action, such as contacting the patient's medical professional, taking a particular action during performance of a surgical procedure, or requesting an updated control algorithm for the drug administration device.

Notifications and feedback can be configured to be transmitted between devices associated with a computing system. In one embodiment, a drug administration app can exchange data with a drug administration device and/or a housing so that a user can configure notification settings of the drug administration device and/or the housing. In at least some embodiments, the drug administration app can be configured to enable a user to configure audible, visual, or tactile notifications.

Figure 15:
FIG. 15 is a schematic view of one embodiment of a user interface.

FIG. 15 illustrates one embodiment of a user interface 1200 displaying data, feedback, and notifications. In the exemplary embodiment illustrated in FIG. 15, the user interface 1200 is associated with a patient administering insulin via a drug administration device to lower the patient's blood sugar, but other types of drugs and other types of drug administration devices can be used as discussed herein.

The user interface 1200 includes a patient identifier 1205, a date/time identifier 1210, a configuration icon 1215, a current conditions portion 1220, a reminder portion 1225, a summary portion 1230, an indication portion 1235, and a received data portion 1240. In at least some embodiments, the layout and arrangement of the identifiers and portions within the user interface 1200 can be interactively rearranged by the user, as will be appreciated by a person skilled in the art. In this way, the user can create a customizable, dashboard-like, display of data that is organized to suit the user's preferences.

The patient identifier 1205 identifies the patient, "Jane Smith." The user interface 1200 is configured to display the user's name after the user has properly authenticated themselves to the respective device or system they are interacting with to help provide a secure system. A user can authenticate their identity in any number of ways, such as by using single-factor, two-factor, multi-factor, and/or strong authentication methods. A user can authenticate their identity using one or more authentication factors such as a password, pass phrases, a personal identification number (PIN), a challenge response, a security question, an ID card, a security token, a software or hardware token, a fingerprint, a retinal pattern, a signature, the user's face or voice, biometric identifiers, and the like. The user can be the patient or other person, such as a medical professional.

The date/time identifier 1210 displays the current date and time. The current date and time may provide the user with temporal context about reminders, notifications, or other schedule based data, such as a reminder when to administer a next dose of a drug.

The configuration icon 1215 is an interactive graphical affordance or icon that, when selected or otherwise activated, causes the user interface 1200 to display additional functionality associated with the settings and configuration of the user interface. Selection/activation of the configuration identifier 1215 is configured to provide a user with tools to configure, not only the display of the user interface 1200, such as the arrangement or ordering of the identifiers and portions within the user interface, but also configurations of the device displaying the user interface 1200. In at least some embodiments, the configuration identifier 1215 is configured to show information indicative of help information regarding correct usage of the patient's drug administration device or housing for which the user interface 1200 is providing information. For example, the configuration identifier 1215 can include an additional graphical affordance or indicator, such as an icon, a symbol, or a number indicating to a user that an update is available to help the user correctly use the patient's drug administration device or housing for which the user interface 1200 is providing information. The indicated update can be associated with an updated version of the software that is available for download and installation on the patient's drug administration device or housing for which the user interface 1200 is providing information. The scope of permissible configuration changes provided by the configuration identifier 1215 can be adjusted as a preference within the system.

The current conditions portion 1220 of the user interface 1200 includes sensor data, e.g., information sensed by sensors, such as sensors 92, 94, 98 of the drug administration device 500 of FIG. 5, one or more sensors that are external to and separate from a drug administration device in a surgical setting in which the user interface 1200 is provided, sensors of a mobile device on which the user interface 1200 is shown, or other sensors. In this example, the current conditions portion 1220 displays the patient's heart rate (78 beats per minute), body temperature (99.1 degrees Fahrenheit), respiration rate (18 breaths per minute), and activity level (6,235 steps toward a goal of 8,000 steps per day).

The reminder portion 1225 provides reminders regarding one or more upcoming drug doses and/or regarding other aspects of the patient's treatment plan. In this example, the reminder portion 1225 provides a reminder to "Administer next dose: Today @ 9:30 pm." Thus, the user is being reminded that the next dose is to be administered in approximately three hours, as the current time is "6:24 pm." Other examples that can be provided in the reminder portion 1225 include reminders indicating a current need to manually administer a dose of the drug to the patient and reminders to change a battery of the patient's drug administration device, to charge the battery of the patient's drug administration device, to order a medication refill for the drug administration device, etc. In at least some embodiments, an audible, tactile, and/or visual notification can be provided in conjunction with a reminder appearing in the reminder portion 1225 to help encourage a user's notice of the newly provided reminder and/or provided at a time a reminded action is due to help encourage performance of the action at the proper time.

The summary portion 1230 provides a summary view of previously scheduled doses of the drug to the patient. As in this illustrated embodiment, the summary portion 1220 can also provide an indication of the intended treatment effect of the drug on the patient, as shown by "1. Previously Scheduled Doses to Lower Blood Sugar." As shown in FIG. 15, the summary portion 1230 includes a list of three previously scheduled doses, items a-c. As shown by item a, the summary portion 1230 indicates that the previously scheduled dose was administered "Today @ 9:30 am," and was successfully delivered ("Completed") on "1/30/19 @ 9:33 am." In this way, the summary portion 1230 provides the user with an intuitive presentation of the timing of the previously delivered doses compared to a predetermined delivery schedule for those doses. As shown by item a, sub-item i, the summary portion 1230 also provides the user with an indication of the estimated remaining duration of the drug's effect on a patient, "Good through: 1/30/19 @ 11:00 pm." Item c also shows information for a delivered dose ("Yesterday @ 9:30 am—Completed 1/29/19 @ 9:26 am"). The previously scheduled doses shown in the summary portion 1230 can also indicate when a patient missed a previously scheduled dose, shown as item b, "Yesterday @ 9:30 pm—Missed." The summary portion 1230 can be configured to allow scrolling to view additional summary information, e.g., doses scheduled for before "Yesterday @ 9:30 am." Other portions of the user interface 1200 can also be configured to allow scrolling for viewing of additional information.

In at least some embodiments, the summary portion 1230 can include other interactive graphical affordances, such as tabs or icons, which, when selected or activated, are configured to cause the summary portion 1230 to display dose delivery data over time in a graphical manner, such as a graph or chart. In at least some embodiments, the dose delivery data included in the summary portion 1230 can be provided in association with other clinical outcomes, sensed data events, and/or self-reported medical condition data provided by the patient. In at least some embodiments, the dose delivery data included in the summary portion 1230 can be provided in association with data received from a computer system such as the system 700 or from other data sources which may be accessible via the system 700 and network 702.

The indication portion 1235 provides a correlation between a timing of a previously delivered dose of the drug to the patient from the drug administration device or the housing and a timing of a medical event experienced by the patient. In this illustrated embodiment, the indication portion 1235 includes a list of the three most recent previously scheduled doses and one or more sensed characteristics of the patient, which in this illustrated embodiment includes the patient's blood sugar level measured at the time of each of the previously scheduled doses, e.g., measured by one of the drug administration device's sensors. When insulin was properly administered ("Completed" in the summary portion 1230) according to the previously scheduled times as shown by doses 1 and 3, the patient's blood sugar levels were kept within a normal range as shown by the measurement of 85 mg/dL corresponding to dose 1 completed "Today @ 9:30 am" and the measurement of 78 mg/dL corresponding to dose 3 completed "Yesterday @ 9:30 am." However, when the patient missed a dose, dose 2, "Yesterday @ 9:30 pm" ("Missed" in the summary portion 1230), the patient's blood sugar level was 225 mg/dL. The indication portion 1235 can be configured to correlate a timing of a previously delivered dose of a drug with a variety of medical events that may be experienced by the patient at the time of the previously delivered dose. In at least some embodiments, the medical event data may originate from the patient's medical records, and the indication portion 1235 can provide a correlation between the timing of previously delivered doses and medical record data, including for example clinical laboratory results.

The received data portion 1240 displays data that may be received from a local surgical hub and/or a remote location, such as the system 700 of FIG. 7 or a remote data source available through the system 700 via network 702 such as a cloud-based system. As shown in FIG. 15, the received data portion 1240 in this illustrated embodiment includes updated medical record information, "1. Updated Medical Records—Now Available." The updated medical record information can be received from an electronic medical records (EMR) database such as an EMR database accessible to a cloud-based system such as the database 1005 of the cloud 1004 of FIG. 9; a medical records database configured within the system 700 of FIG. 7; and/or a database associated with a computer system located at medical facility 706 of FIG. 7. In an exemplary embodiment, a user may view the updated medical records by clicking or otherwise selecting a uniform resource locator (URL) that the user interface 1200 has provided. In this illustrated example, clicking the word "here" as shown in "b. Click here to view" is configured to cause the user interface 1200 to provide the updated medical records for display. URLs may be used without limit within the user interface 1200 to provide additional data for display to the user.

As also shown in the received data portion 1240, a user may receive data providing help information about the usage of the drug administration device and/or the housing. For example, the received data portion 1240 can provide an indication of the help information as update information, which in this illustrated embodiment is shown as "2. New Device Software—Available for Download." The help information can include new device configuration settings as well as product documentation, such as a user's manual associated with the patient's drug administration device or housing. A user may cause the help information to be transmitted to and installed on the drug administration device or the housing by clicking or otherwise selecting the configuration identifier 1215.

The received data portion 1240 can include data which may be received from a server based on information sensed or determined by the patient's drug administration device. For example, the received data portion 1240 in this illustrated embodiment includes received data as "3. Compliance Message from Dr. Jones." Based on the patient's drug administration device and/or housing sensor(s) sensing the elevated blood sugar level of 225 mg/dL, which occurred in relation to the drug dosage previously scheduled and not administered "Yesterday @ 9:30 pm," the drug administration device and/or housing can transmit the sensed blood sugar levels (in addition to the drug delivery and compliance data) for display on the user interface 1200 in the received data portion 1240. In this illustrated example, as a result of receiving the sensed blood sugar values (in addition to summary data indicating the missed dosage scheduled for "Yesterday @ 9:30 pm"), the system may notify the patient's medical professional to send a compliance message to the patient to remind the patient, e.g., via notification in the reminder portion 1225, of the appropriate guidance and drug administration schedule necessary to reduce the patient's elevated blood sugar levels. In this way, data that is sensed or otherwise determined by the patient's drug administration device or housing can be transmitted to a remote computer system and/or a local surgical hub, where upon receiving the sensed information, the remote computer system and/or local surgical hub can be configured to generate and transmit data associated with the sensed information back to the drug administration device or housing to be provided to a user via the user interface 1200.

Additional descriptions of data and displays of data provided within a user interface, such as user interface 80 of a drug administration device 500 or housing 630 or user interface 2080 of drug administration device 2002, are provided in U.S. Pat. Pub. No. 2002/0091454 entitled "Remotely Programmable Infusion System" published Jul. 11, 2002 and U.S. Pat. Pub. No. 2008/0139907 entitled "Intelligent Personal Health Management Appliance For The Measurement And Monitoring Of Health Factors And Controlled Delivery Of Drugs" published Jun. 12, 2008, which are hereby incorporated by reference in their entireties.

Devices and systems disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

It can be preferred that devices disclosed herein be sterilized before use. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 issued Feb. 14, 2012 and entitled "System And Method Of Sterilizing An Implantable Medical Device." It is preferred that device, if implanted, is hermetically sealed. This can be done by any number of ways known to those skilled in the art.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical system, comprising:
    a surgical hub including a communications interface configured to wirelessly receive data during performance of a surgical procedure; and
    a drug administration device configured to deliver a drug therefrom to a patient, the drug administration device including:
        a sensor configured to sense information relating to a condition of the patient,
        a memory configured to store data therein, the stored data including a key established with a surgical hub and that is unique to the drug administration device and the surgical hub,
        a communications interface configured to wirelessly transmit data indicative of the sensed information to the communications interface of the surgical hub, and
        a processor configured to use the key to anonymize the data indicative of the sensed information prior to the transmission of the data indicative of the sensed information.

2. The system of claim 1, wherein the condition is at least one of a physiological condition of the patient and a situational condition of the patient.

3. The system of claim 1, wherein the condition is at least one of blood sugar level, blood pressure, perspiration level, heart rate, core temperature, tremor detection, time of day, date, patient activity level, blood pressure, metabolic rate, altitude, temperature of the drug, viscosity of the drug, geographic location information, angular rate, current of a motor used in delivering the drug, blood oxygenation level, sun exposure, osmolality, and air quality.

4. The system of claim 1, wherein the condition is at least one of a geographic location of the patient and an orientation of the patient.

5. The system of claim 1, wherein the condition is at least one of a condition of the drug administration device and a condition of the drug.

6. The system of claim 1, wherein the condition includes intake of food and/or drink by the patient.

7. The system of claim 6, wherein the memory is also configured to store therein an algorithm including at least one variable parameter; and
the processor is also configured to:
    control delivery of a first dose of the drug from the drug administration device to the patient by executing the algorithm,
    change the at least one variable parameter of the algorithm stored in the memory based on the data gathered by the sensor regarding the intake of food and/or drink by the patient so a second dose of the drug is coordinated with a meal time of the patient, and
    after changing the at least one variable parameter, control delivery of the second dose of the drug from the drug administration device to the patient by executing the algorithm.

8. The system of claim 1, wherein the communications interface of the drug administration device is configured to transmit the data during the performance of the surgical procedure; and
    the surgical hub also includes a processor configure to analyze, during the performance of the surgical procedure, the data received by the communications interface of the surgical hub.

9. The system of claim 8, wherein the processor of the surgical hub is configured to provide, during the performance of the surgical procedure, a notification to a user of the surgical hub indicative of the analysis.

10. The system of claim 9, wherein the condition is at least one of a physiological condition of the patient and a situational condition of the patient; and
    the notification indicates that the data exceeds a predetermined threshold for the condition.

11. The system of claim 1, wherein the processor of the drug administration device is configured to provide a notification to a user of the drug administration device; and
    the notification indicates that the data exceeds a predetermined threshold for the condition.

12. The system of claim 1, wherein the surgical hub includes a server configured to be located local to, external to, and separate from the drug administration device.

13. The system of claim 1, wherein the communications interface of the surgical hub is configured to wirelessly transmit data indicative of the received data to a cloud-based server configured to be remotely located from the drug administration device and from the surgical hub, the cloud-based server including a communications interface configured to receive the data transmitted by the communications interface of the surgical hub.

14. The system of claim 1, wherein the drug administration device is configured to deliver the drug therefrom to the patient during performance of the surgical procedure on the patient;
    the sensor is configured to sense information relating to the condition of the patient during the performance of the surgical procedure; and
    the communications interface is configured to wirelessly transmit the data indicative of the sensed information to the communications interface of the surgical hub during the performance of the surgical procedure.

15. A surgical method, comprising:
    sensing, using the sensor of claim 1, the information relating to the condition of the patient;
    anonymizing, using the processor of claim 1, the data indicative of the sensed information;
    wirelessly transmitting, using the communications interface of claim 1, the anonymized data to the surgical hub of claim 1.

* * * * *